US010138264B2

(12) United States Patent
Brown

(10) Patent No.: US 10,138,264 B2
(45) Date of Patent: Nov. 27, 2018

(54) RECOMBINED MOLECULES AND PREPARATION THEREOF

(75) Inventor: Dennis M. Brown, Menlo Park, CA (US)

(73) Assignee: VALENT TECHNOLOGIES LLC, Menlo Park, CA (US)

( * ) Notice: Subject to any disclaimer, the term of this patent is extended or adjusted under 35 U.S.C. 154(b) by 0 days.

(21) Appl. No.: 13/039,055

(22) Filed: Mar. 2, 2011

(65) Prior Publication Data

US 2011/0312034 A1 Dec. 22, 2011

Related U.S. Application Data

(63) Continuation of application No. 10/843,148, filed on May 10, 2004, now abandoned.

(60) Provisional application No. 60/490,804, filed on Jul. 29, 2003, provisional application No. 60/484,214, filed on Jul. 1, 2003, provisional application No. 60/468,894, filed on May 8, 2003.

(51) Int. Cl.
| | | |
|---|---|---|
| C12P 17/18 | (2006.01) | |
| C12P 19/26 | (2006.01) | |
| C40B 50/00 | (2006.01) | |
| C07H 17/08 | (2006.01) | |
| C07H 21/04 | (2006.01) | |
| C07K 1/04 | (2006.01) | |
| C07K 1/107 | (2006.01) | |
| C07K 9/00 | (2006.01) | |
| C12P 1/00 | (2006.01) | |
| C12P 7/44 | (2006.01) | |
| C12P 7/46 | (2006.01) | |
| C12P 13/04 | (2006.01) | |
| C12P 17/04 | (2006.01) | |
| C12P 19/00 | (2006.01) | |

(52) U.S. Cl.
CPC ............ *C07H 17/08* (2013.01); *C07H 21/04* (2013.01); *C07K 1/047* (2013.01); *C07K 1/1077* (2013.01); *C07K 9/00* (2013.01); *C12P 1/00* (2013.01); *C12P 7/44* (2013.01); *C12P 7/46* (2013.01); *C12P 13/04* (2013.01); *C12P 17/04* (2013.01); *C12P 19/00* (2013.01)

(58) Field of Classification Search
CPC ........... C40B 30/00; C12P 19/44; C12P 17/04
USPC .................................. 506/7; 435/74
See application file for complete search history.

(56) References Cited

U.S. PATENT DOCUMENTS

| | | | |
|---|---|---|---|
| 5,288,514 A | 2/1994 | Ellman | 427/2 |
| 5,549,974 A | 8/1996 | Holmes et al. | 428/403 |
| 5,869,295 A | 2/1999 | LaBean et al. | 435/91.2 |
| 6,369,252 B1 | 4/2002 | Akoh | 554/227 |
| 6,448,443 B1 * | 9/2002 | Schreiber et al. | 506/9 |
| 6,489,145 B1 * | 12/2002 | Short | 506/1 |
| 2003/0133997 A1 | 7/2003 | Choi et al. | 424/725 |
| 2003/0166177 A1 | 9/2003 | Dordick et al. | 435/132 |
| 2011/0118126 A1 | 5/2011 | Hansen et al. | |

FOREIGN PATENT DOCUMENTS

| | | |
|---|---|---|
| EP | 0 774 464 | 5/1997 |
| WO | WO 96/03424 | 2/1996 |
| WO | WO 97/22594 | 6/1997 |
| WO | WO 97/35199 | 9/1997 |
| WO | WO 97/40034 | 10/1997 |
| WO | WO 9935288 A1 * | 1/1998 |
| WO | WO 9964032 A1 * | 12/1999 |
| WO | WO 02/07870 | 1/2002 |
| WO | WO 02074929 A2 * | 9/2002 |

OTHER PUBLICATIONS

Baltz (Chapter 15. Molecular Genetic and Combinatorial Biology Approaches to Novel Antibiotics, Antibiotic Development and Resistance, Huges and Anderssor Eds., 2001, 233-250).*
Geysen et al., Combinatorial Compound Libraries for Drug Discovery: An Ongoing Challenge, Nature Reviews, Drug Discovery, 2003, 2, 222-230.*
Agrafiotis et al., Combinatorial Informatics in the Post-Genomics Era, Nature Reviews, Drug Discovery, 2002, 1, 337-346.*
Normark et al., Evolution and Spread of Antibiotic Resistance, Journal of Internal Medicine, 2002, 252, 91-106.*
Kotra et al., Aminoglycosides: Perspectives on Mechanisms of Action and Resistance and Strategies to Counter Resistance, Anitmicrobial Agents and Chemotherapy, 2000, 44(12), 3249-3256.*
McCafferty et al., Synergy and Duality in Peptide Antibiotic Mechanisms, Current Opinion in Chemical Biology, 1999, 3, 672-680.*
Kamerbeek et al., Baeyer-Villiger Monooxygenases, An Emerging Family of Flavin-Dependent Biocatalysts, Chapter 7, Adv. Synth. Catal., 2003, 6+7, 105-120. (Year: 2003).*
Koeller et al., Enzymes for Chemical Synthesis, Nature, 2001, 409, 232-240. (Year: 2001).*
Fenniri, H., "Recent advances at the interface of medicinal and combinatorial chemistry views on methodologies for the generation and evaluation of diversity and application to molecular recognition and catalysis," *Curr. Med. Chem.* 3(5):343-378 (1996).
Fauchere, J.-L., et al., "Combinatorial chemistry for the generation of molecular diversity and the discovery of bioactive leads," *Chemomet. Intell. Lab. Systs.* 43(1&2):43-68 (Sep. 1998).
Gordon, E., et al., *Combinatorial chemistry and molecular diversity in drug discovery*, pp. 3-39, John Wiley & Sons, Inc.: New York, NY (1998).
Morgan, J., et al., "Synthesis of biomimetic marine natural products via enzymatic and microbial biotransformations," *Abs. Pap. Am. Chem. Soc.* 219(1-2):BIOT 9 (2001).

(Continued)

*Primary Examiner* — Amy M Bunker
(74) *Attorney, Agent, or Firm* — Ditthavong & Steiner, P.C.

(57) ABSTRACT

The invention relates to novel molecules and libraries thereof as well as methods for their production. Methods of producing the novel molecules include the cleaving of starting molecules into molecular subunits and the assembly of the subunits into novel recombined molecules.

2 Claims, 14 Drawing Sheets

(56) References Cited

OTHER PUBLICATIONS

Ness, J., et al., "Synthetic shuffling expands functional protein diversity by allowing amino acids to recombine independently," *Nat. Biotechnol.* 20:1251-1255 (2002).
Park, C.B., et al., "Biocatalyst engineering for synthesis and screening of chemical libraries," *Abs. Pap. Am. Chem. Soc.* 224(1-2):BTEC 17 (2002).
Schuster, et al., "Solid-Phase-Chemical-Enzymatic Synthesis of Glycopeptides and Oligosaccharides," J. Am. Chem. Soc. v. 116, p. 1135-1136, 1994.
Segundo, F., et al., "A combinatorial biocatalysis approach to an array of cholic acid derivatives," *Biotechnol. Bioeng.* 81(4):391-396 (Feb. 2003).
Comer et al. J. Med. Chem. 2014,57 (20), pp. 8496-8502.
Erlanson, D. A. Top. Curr. Chem. 2012, 317, pp. 1-32.
Faber, K. *Biotransformations in Organic Chemistry: A Textbook*, 4th ed.; Springer, 2000; table of contents.
Okano et al. in J. Am. Chem. Soc. 2014, 136 (39), pp. 13522-13525.
Smith, M. B.; March, J. *March's Advanced Organic Chemistry: Reactions, Mechanisms, and Structure*, 5th ed.; Wiley, 2001; table of contents.
Silverman, R. B. The Organic Chemistry of Enzyme-Catalyzed Reactions; Academic Press, 2002; table of contents.

\* cited by examiner

Step 1.

Step 2.

Step 3:

Step 4:

Step 5:

Degradation reactions

Chemical reactions:

R = H, or alkyl or aryl.

Any double bond:

Any ester:

Any carbonyl:

Biological reactions:

Carbonyl:

Esters:

Amides:

K. Faber in: Biotransformations in Organic Chemistry, 4th edition

RECOMBINED MOLECULES AND PREPARATION THEREOF

This application claims the benefit of U.S. Application Ser. No. 60/490,804, filed Jul. 29, 2003; U.S. Application Ser. No. 60/484,214, filed Jul. 1, 2003; and U.S. Application Ser. No. 60/468,894, filed May 8, 2003, each of which is incorporated by reference in their entirety.

TECHNICAL FIELD

The invention relates to novel molecules and libraries thereof as well as methods for their production.

BACKGROUND OF THE INVENTION

The creation of diverse chemical structures for efficient biological evaluation and drug screening remains of great importance for the discovery of biologically useful molecules. The efficient creation of molecules with drug-like properties that are also novel compositions or chemical structures is critical if investments for improvements in disease management are to be made.

The identification of small organic molecules that affect specific biological functions is an endeavor that impacts both biology and medicine. Such molecules are useful as therapeutic agents and as probes of biological function. The interaction of small molecules with biological targets and their ability to affect specific biological functions, may also serve as candidates for the development of therapeutics.

Because it is difficult to predict which small molecules will interact with a biological target, intense efforts have been directed towards the generation of large numbers, or libraries of small organic compounds with drug-like pharmaceutical properties. These libraries can then be evaluated in sensitive screens to identify active molecules. In many cases, researchers have developed biased libraries, in which all members share a particular characteristic, such as an ability to interact with a particular target ligand, or a characteristic structural feature designed to mimic a particular aspect of a class of natural compounds. For example, a number of libraries have been designed to mimic one or more features of natural peptides. Such peptidomimetic libraries include phthalimido libraries (WO97/22594), thiophene libraries (WO97/40034), benzodiazopene libraries (U.S. Pat. No. 5,288,514) libraries formed by the sequential reaction of dienes (WO96/03424), thiazolidone libraries, libraries of metathiazanones and their derivatives (U.S. Pat. No. 5,549,974), and azatide libraries (WO 97/35199), isonicotinamide based libraries (U.S. Pat. No. 6,448,443).

Recognizing the need for the development of synthetic strategies that produce large numbers of complex molecules, Boger et al. (EP0774 464) have recently developed a solution-phase synthetic strategy for producing a library of compounds based on a functionalizable template core, to which various reagents can be added. However, there remains a need for development of solid-phase strategies, where the more rapid production methods such as split-and-pool strategies can be employed to generate larger, more complex libraries. Additional solution phase strategies would also be valuable.

Each of the libraries described has provided solid synthetic strategies for compounds possessing specific core functionalities, but none achieves the complexity of structures found in natural products, or in other lead compounds prepared through traditional chemical synthetic routes. Complex natural products have been the source of important pharmaceutical products for the treatment of a host of human diseases and medical conditions. The natural products commonly contain several different functionalities and often are rich in stereochemical complexity. Such diversity and complexity are often difficult to achieve if the synthesis is restricted to a specific class of compounds. In other situations there are limitations in the ability to create analogs over a broad range of lipophilicities, reactivities, stereocomplexities, etc.

In addition, exploiting the diversity and structural complexity of chemical structures from natural products remains a significant goal of medicinal chemists and pharmaceutical corporations. The value of agents of natural product plant origin such as the taxanes, camptothecins, vinca alkaloids, ellipticines, podophyllotoxins, mithramycins, steroids, agents from fermentations such as phleomycins, bleomycin, doxorubicin, vancomycin, penicillin, streptomycins, erythromycins, rapamycins, actinomycins, avermectins, phomopsin, cytochalasins, etc., are some examples which have been of importance for the treatment of life-threatening diseases. Rational exploration of analogs, hybrids, substructures, fragments and variants of these and other complex scaffold structures should be of significant utility in the drug discovery and development process. Moreover, application of more efficient methods of creation of novel chemical structures from such sources and others would increase the chemical space and structural diversity that is extremely important for the identification of potential novel therapeutics.

Thus, a need exists for methods of generating complex libraries of novel molecules useful in the generation of therapeutics.

SUMMARY OF THE INVENTION

In accordance with the objects outlined above, the present invention provides novel molecules and libraries thereof, as well as methods for their production. One aspect of the invention provides for methods of generating molecular subunits by cleaving a starting molecule. In preferred embodiment, the cleaving is performed enzymatically. In a further preferred embodiment, the enzyme used to perform the cleaving step is selected from the group consisting of hydrolases, oxidases, reductases, proteases, peptidases, esterases, and mono-oxygenases. In a further preferred embodiment, the starting molecule is selected from the group consisting of the group consisting of small molecules, polypeptides, peptidomimetics, nucleic acids, alkaloids, macrolides, terpenes, macrocycles, fermentation products, or molecules from plant, animal, bacterial, or fungal sources.

A further aspect of the invention provides for a method comprising cleaving one or more starting molecules into molecular subunits and assembling two or more of the subunits to produce at least one recombined molecule which is different from the starting molecule(s). In a preferred embodiment, at least one of the cleaving or assembling steps is mediated by an enzyme. The cleavage step is preferably mediated by an enzyme selected from the group consisting of hydrolases, oxidases, reductases, proteases, peptidases, esterases, mono-oxygenases, lyases and ligases. The assembly step is preferably mediated by an enzyme selected from the group consisting of lyases, ligases, fumarases, glycosyl transferases, glycosidases, haloperoxidases and halohydrin eposidases. In a further preferred embodiment, at least one of the recombined molecules is not a recombined nucleic acid or recombined protein. In yet a further preferred embodiment, the cleaving step is of two or more different starting molecules and the recombined molecule or molecules comprise intermolecular combinations of subunits from the different molecules. In yet a further preferred embodiment, the recombined molecules or molecules are modified. In additional embodiments, the starting molecules are attached to a solid support.

In a further preferred embodiment the starting molecules used to produce the molecular subunits are selected from the group consisting of polypeptides, nucleic acids, alkaloids, macrolides, terpenes, macrocycles, fermentation products, and molecules from plant, animal, bacterial, and fungal sources. Preferably, at least one of the starting molecules is selected from the group consisting of vancomycin, Rifamycin B, erythromycin, camptothecin, 9-hydroxyellipticine, bisamidophthalanide derivatives, rapamycin, actinomycinD, avermectin B1, phomopsin A, and cytochalasin D.

A further aspect of the invention provides for screening for a biological activity of the recombined molecule. In a preferred embodiment, the screen comprises contacting the recombined molecule with a biological target, and determining the effect of the recombined molecule on a property of the biological target.

A further aspect of the invention provides for a library of recombined molecules made according to the methods described herein.

A further aspect of the invention provides for a method for screening for a biologically active recombined molecule comprising contacting the library of recombined molecules with a biological target and determining the effect of the library on a property of the biological target. In a preferred embodiment, the library is partially purified prior to contacting with a biological target.

A further aspect of the invention provides for isolating from the library a recombined molecule with biological activity. In a preferred embodiment, the structure of the recombined molecule with biological activity is identified.

A further aspect of the invention provides for a biologically active recombined molecule made according to the methods described herein.

A further aspect of the invention provides for a method comprising cleaving one or more starting molecule(s) into molecular subunits, modifying the molecular subunits, and assembling two or more modified molecular subunits to produce at least one recombined molecule which is different from said starting molecule(s). In a preferred embodiment, at least one of the cleaving or assembling steps is mediated by an enzyme. The cleavage step is preferably mediated by an enzyme selected from the group consisting of hydrolases, oxidases, reductases, proteases, peptidases, esterases, monooxygenases, lyases and ligases. The assembly step is preferably mediated by an enzyme selected from the group consisting of lyases, ligases, fumarases, glycosyl transferases, glycosidases, haloperoxidases and halohydrin eposidases. In a further preferred embodiment, at least one of the recombined molecules is not a recombined nucleic acid or recombined protein.

DETAILED DESCRIPTION

Figure 1:
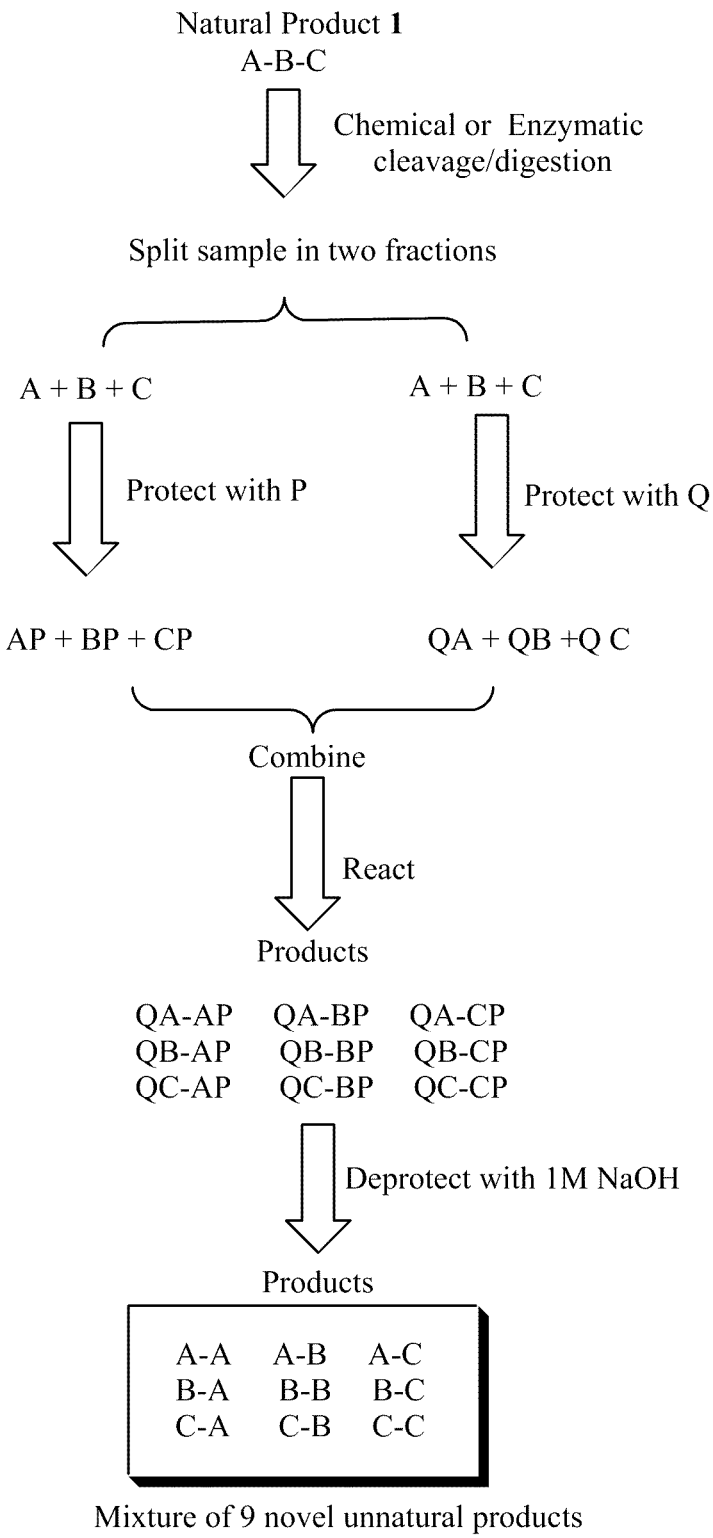
FIG. 1 depicts a general scheme for cleaving of a starting molecule.

The present invention is directed toward compositions and methods useful in the generation of novel molecules. This invention involves the breaking or cleavage of chemical bonds of molecules such that the resulting molecular subunits can be evaluated for biological activity or assembled with other molecular subunits of the same or different molecules to create recombined molecules. A variety of chemical and biochemical approaches can be used for molecular cleavage and subunit assembly. These techniques include common and unique organic synthetic procedures, as well as biochemical techniques including the use of purified enzymes, enzyme extracts, and whole cell fermentations for the creation of novel molecular subunits, and for the assembly of one or more subunits to form recombined molecule(s), at least one of which has a unique chemical structure as compared to the starting molecules. Furthermore, additional groups such as chemical functional groups, coupling agents and linkers may be covalently linked to the molecular subunits before assembly or to the recombined molecule. The recombined molecules can form libraries suitable for biological screening. The methods of the invention also find use in large scale synthesis. In some cases, a combinatorial split and mix approach is employed for the creation of additional chemical variants. Variations of the invention include the use of solid-phase supports during the cleaving and/or assembly steps used to make recombined molecules.

Molecular Subunits

One aspect of the invention provides for methods of cleaving one or more starting molecules to produce molecular subunits. By "cleaving" is meant the breaking of one or more chemical bonds of a starting molecule(s) to form molecular subunits. In a preferred embodiment the cleaving is performed enzymatically. The enzymes used to cleave the molecule are from purified sources (e.g. naturally occurring or made recombinantly), from extracts from bacterial, fungal, yeast, plant, or mammalian cell sources, or are genetically engineered enzymes or spontaneous mutated enzymes with enhanced activity or modified specificity. Tissues or cell cultures with specific infections (e.g., plant rusts) may also be used for the production of unique enzyme systems to react with or modify molecules or molecular subunits. Enzymes useful in the cleaving of molecules include, but are not limited to, enzymes involved in group transfer reactions, hydrolases, oxidases, reductases, proteases, peptidases, esterases, mono-oxygenases, enzymes involved in substitution reactions, enzymes involved in electrophilic or nucleophilic addition, and enzymes involved in decarboxylation. Examples of enzymes useful in this group comprise pig liver esterase (PLE), horse liver esterase (HLE), acetylcholine esterase (ACE), carbonylesterase NP, alpha-chymotrypsin, subtilisin, trypsin, pepsin, papain, penicillin acylase, porcine pancreatic lipase (PPL), formate dehydrogenase (FDH), ethanol and alcohol dehydrogenase (ADH), yeast alcohol dehydrogenase (YADH), horse liver alcohol dehydrogenase (HLDH), glucose dehydrogenase (GDH), enolate reductases, oxidoreductases, mono-oxygenases including cytochrome p450 dependent mon-oxygenases and flavin-dependent mono-oxygenases, soybean lipoxygenase, alpha oxidases, aldehyde dehydrogenases, horseradish peroxidase, chloroperoxidase (CPO), bromoperoxidases, etc. The enzymes used to cleave the molecule may be purified enzymes, enzyme extracts or may be present in whole cells In a further preferred embodiment the cleaving is performed chemically. Chemical reactions useful for cleaving bonds include, but are not limited to, chemical hydrolysis, reductions, oxidations, ozonolysis, decarboxylation, electrophilic additions, nucleophilic additions, etc.

In further preferred embodiments the cleavage is performed by methods such as photolysis, UV irradiation, or heat-induced cleaving of molecules.

After the starting molecule or molecules are cleaved, the resulting molecular subunits can be evaluated for their chemical structure(s) and properties, as well as their potential biological activities. In some embodiments, determination of subunit activity can be used to select one or more subunits from the same or different molecule for assembly into a recombinant molecule. However, such screening is not necessary to practice the invention. A "biologically active" molecular subunit refers to a molecular subunit that binds to or modulates a biological target. Biological activity of the molecular subunits can be determined by a variety of assays well known in the art. Assays useful in determining biological activity include, for example, binding assays; assays to determine changes in biological target function, cellular physiology, cellular viability, and cellular growth characteristics; immunological assays; and assays to determine alteration of nucleic acid and protein expression.

In a preferred embodiment of the invention, the molecular subunit is selected from the molecular subunits shown in any of FIGS. 2-12.

In a preferred embodiment, an initial screen for biological activity of a molecular subunit comprises contacting the molecular subunit with a biological target. Examples of biological targets include, but are not limited to, whole cells, cellular extracts, receptor ligands, proteins (e.g. receptors and enzymes), and nucleic acids. A biological target may comprise more than one component. Multi-component biological targets include, for example, protein-protein binding partners, nucleic acid-nucleic acid binding partners, protein-nucleic acid binding partners, cellular pathways, and membrane channels.

One embodiment of the invention provides for a method of screening for a molecular subunit capable of binding to a biological target. In preferred binding assays, either the molecular subunit or the biological target is labeled with a fluorescent, a chemiluminescent, a chemical moiety, or a radioactive signal, to provide a means of detecting the binding of the molecular subunit to the biological target. The label also can be an enzyme, such as, alkaline phosphatase or horseradish peroxidase, which when provided with an appropriate substrate produces a product that can be detected. Alternatively, the label can be a labeled compound or small molecule, such as an enzyme inhibitor, that binds but is not cleaved or altered by the enzyme. The label also can be a moiety or compound, such as, an epitope tag or biotin which specifically binds to streptavidin. For the example of biotin, the streptavidin is labeled as described above, thereby, providing a detectable signal for the bound molecular subunit. As known in the art, unbound labeled streptavidin is removed prior to analysis. Alternatively, the molecular subunit can be immobilized or covalently attached to a surface and contacted with a labeled biological target.

Another embodiment provides for methods of screening for a biologically active molecular subunit that modulates a property of a biological target. Assays useful in screening for biologically active molecular subunits that modulate a property of a biological target include cell growth and mortality assays (including assays to determined antimicrobial and antiproliferative activity), whole organism growth and mortality assays, protein binding assays, enzyme inhibition/activation assays, immunological assays, biochemical assays, and transcription and translations assays.

Another embodiment provides for screening for molecular subunits that modulate expression levels of genes. The most classical technique used to assess in vivo gene expression is to introduce a gene to the genome of a test animal. These introduced genes (transgenes) are engineered to contain promoters that are constitutively or inducibly active in the tissue of choice placed upstream from the coding sequence of the gene product. A second sequence coding for an easily assayed or visualized protein (reporter gene) is included immediately downstream from the transgene. The transcription of both the transgene and reporter gene is driven by the same promoter, therefore expression occurs in the same tissues. Assessment of the expression of the routine and more easily measured reporter is used to verify the tissue-specific and/or drug influenced expression of the transgene. Changes in the expression of the reporter gene results from treatment of the cells with molecular subunits which influence gene expression. Once the assay is run, the data is analyzed to determine the expression levels, and changes in expression levels as between states, of individual genes, or individual proteins, forming an expression profile.

The reactions outlined herein may be accomplished in a variety of ways, as will be appreciated by those in the art. Components of the reaction may be added simultaneously, or sequentially, in any order, with preferred embodiments outlined below. In addition, the reaction may include a variety of other reagents may be included in the assays. These include reagents like salts, buffers, neutral proteins, e.g. albumin, detergents, etc which may be used to facilitate optimal hybridization and detection, and/or reduce non-specific or background interactions. Also reagents that otherwise improve the efficiency of the assay, such as protease inhibitors, nuclease inhibitors, anti-microbial agents, etc., may be used, depending on the sample preparation methods and purity of the target. In addition, either solid phase or solution based (i.e., kinetic PCR) assays may be used.

Recombined Molecules

Another aspect of the invention provides for methods of cleaving one or more starting molecules to produce molecular subunits and assembling one or more of the molecular subunits to produce a recombined molecule or recombined molecules. In one embodiment, subunits from the same starting molecule are assembled to form at least one recombined molecule. In this case, the recombined molecule is different from the starting molecule. In this embodiment, the recombined molecule is composed of subunits from the starting molecule but has a different structure, and preferably different properties, as compared to the starting molecule. The recombined molecule may contain all of the molecular subunits of the starting molecule (but in the form of a different structure) or less than all of the molecular subunits of the starting molecule.

A further aspect of the invention provides for methods of cleaving two or more different starting molecules into molecular subunits and assembling two or more of the resulting molecular subunits to produce a recombined molecule or molecules. At least one of the recombined molecule(s) is different from the starting molecules.

By "assembled", "assembling", or "assembly" is meant the formation of one or more covalent bonds between molecular subunits to produce a recombined molecule or molecules. In one embodiment, the assembly is a result of an unmediated chemical reaction. In a further preferred embodiment, the assembly is mediated enzymatically. Enzymes useful in mediating the assembly of molecular bonds belong to the class of lyases, comprising aldolases, transketolases, hydroxynitrile lyases, and enzymes that mediate acyloin reactions. Additional enzymes useful in mediating the assembly of molecular bonds include ligases, fumarases, glycosyl transferases, glycosidases, haloperoxidases and halohydrin eposidases. In yet a further preferred embodiment, the assembly is chemically mediated, for example, by a coupling reagent or chemical cross-linker. Coupling reagents useful in assembly of the molecular subunits include carbodiimides (for example lethyl-3-(3' dimethyl; aminopropyl) carbodiimide; dicyclohexylcarbodiimde, etc.), benzotriazoles (for example, [benzotriazole-1-yl-oxy (dimethylamino)-phosphoniumhexafluorophosphate; 2-(1H-benzotriazole-lyl)-1,1,3,3-tetreamethyluronium hexafluorophosphate, N-hydroxybenzotriazole, etc.), 1,1'-carbony-diimidazoles, 4-dimethylaminopyridine, N,N'-disuccinimidyl carbonate, N-hydroxy-5-norbornene-endo-2,3-dicarboximide, N-hydroxysuccinimide, 1-(mesitylene-2-sulfonyl)-3-nitro-1H-1,2,4-triazole, and other agents well known in the art (see 1994 Pierce Chemical Company catalog, technical section on cross-linkers, pages 155-200, hereby expressly incorporated by reference). In a preferred embodiment the enzyme or chemical mediator is attached to a solid support.

In a preferred embodiment, the molecular subunits resulting from the cleaving of the starting molecules are split into at least two separate groups or pools of molecular subunits. Each pool is then exposed to a chemical agent that adds a protective group to the reactive groups in the molecular subunits. The protected molecular subunits are no longer able to react with other subunits in the pool via the reactive groups. The term "protective group" as used herein, refers to a chemical group that reacts selectively with a desired functionality to give a derivative that is stable to further reactions for which protection is desired, can be selectively removed from the particular functionality that it protects to yield the desired functionality, and is removable by reagents compatible with the other functional group(s) generated during the reactions. In a preferred embodiment, each pool is treated with a different chemical agent. Two or more of the pools of protected molecular subunits are then mixed to form a mixture of protected subunits. The subunits may then be assembled followed by the deprotection. Alternatively, the protective groups are removed from the subunits and the unprotected molecular subunits assemble to form recombined molecules. Chemical agents that are useful in the practice of the invention include, but are not limited to, acylating agents, such as acetic anhydride, and methylating agents, such as trimethylsilyl diazomethane ($TMSCHN_2$) and AcCl/MeOH. Additional chemical agents and protective groups useful in the invention are discussed in Greene and Wuts, "*Protective Groups in Organic Synthesis*", $2^{nd}$ ed., John Wiley and Sons, Inc. (1991), herein incorporated by reference.

In a preferred embodiment, one or more of the protective groups is attached to a solid support. The term "solid support", as used herein refers to beads, solid surfaces, substrates, particles, pellets, disks, capillaries, pore-glass beads, silica gels, polystyrene beads optionally cross-linked with divinylbenzene, grafted co-poly beads, latex beads, dimethylacrylamide beads optionally cross-linked with N,N'-bis acryloyl ethylene diamine, glass particles coated with a hydrophobic polymer, or any other material having a rigid or semi-rigid surface. These materials also contain functionalities such that starting molecules, molecular subunits and recombined molecules may be attached to them.

Another aspect of the invention provides for recombined molecules produced by the methods described herein. In a preferred embodiment, the recombined molecules are biologically active. A "biologically active" recombined molecule refers to a recombined molecule that binds to or modulates a biological target. As discussed further below, biological activity of the recombined molecules can be determined by a variety of assays well known in the art.

In a preferred embodiment of the invention, the recombined molecule is selected from the recombined molecules shown in any of FIGS. 5-12.

Preferably, the recombined molecules possess characteristics in common with the starting molecules used to produce them. For example, in some embodiments the recombined molecules contain at least one stereocenter, a high density and diversity of functionality displayed in a radial array, and a diverse range of atoms within one structure. In this context, diversity of functionality can be defined as varying a specific characteristic or set of characteristics of the functional groups present in the recombined molecule including, but not limited to, topology, size, charge, hydrophobicity, hydrophilicity, and reactivity. Such functional groups include those made or remaining after assembly as well as functional groups added to the molecular subunits before or during assembly or the addition of functional groups after assembly of the recombined molecule. Examples of ways in which functional groups may differ from one another include, but are not limited to, variations in either the shape or chain length of a collection of atoms or variations in the particular atoms present in the functional groups. Additionally, functional groups may also differ from one another by variations in both the shape or chain length and variations in the particular atoms present in the functional groups. A high density of functionality refers to a large number of chemical moieties present in the recombined molecule library member.

In some embodiments, the functional groups of the molecular subunits and recombined molecules are displayed in a radial array. This configuration enables diversification in all directions, thus adding to the complexity of the molecular subunits and recombined molecules.

In one embodiment, the molecular subunits are purified before they are assembled into recombined molecules. The purification steps may be used to isolate a specific molecular subunit or subunits. The isolated molecular subunit or subunits can be analyzed for chemical structure and biological properties as discussed above. The isolated molecular subunit or subunits can be assembled to produce recombined molecules as discussed above.

In a further preferred embodiment, the molecular subunits are modified before they are assembled into recombined molecules. Modifications include the introduction of new functionalities such as, side chains, linkers, reactive intermediate moieties, etc. using synthetic chemistry or biochemical/enzymatic approaches. The following reactions are used to modify molecular subunits of recombined molecules: alkylation, arylation, halogenation, esterification, enolization, nitration, carboxylation, sulfonation, phosphorylation, oxygenations, amidations, aminations, glycosylations, etc. Modifications may also include the addition of linkers and bifunctional linkers to facilitate assembly. In a preferred embodiment, modifications are introduced enzymatically. Enzymes and enzyme include but are not limited to those involved in group transfer reactions, aminations, phosphorylations, mono and dioxygenation. In a further preferred embodiment, modifications are introduced chemically. Chemical modifications include nucleophilic and electrophilic additions, (SN1, SN2, SNAr, SN2', E1, E2 etc), carboxylations, and Aldol, Claisen and Michael reactions, formylations, methylations, and hydroxymethylations, etc.

In yet a further aspect of the invention, the recombined molecule or recombined molecules can be further modified. As discussed above, modifications include the introduction of new functionalities, side chains, linkers, reactive intermediate moieties, etc. using synthetic chemistry or biochemical/enzymatic approaches. Additional modifications of these structures can be initiated to broaden the diversity and uniqueness of the recombined molecules. Such modifications include, but are not limited to, isomerizations (cis/trans), rearrangements, cyclizations, the use of radical intermediates, hydrogen shifts, enolization, aza-allylic modifications, salt formation, etc.

One aspect of the invention provides for methods of screening the recombined molecules for biological activity. The biological activity of the recombined molecules can be determined by a variety of assays as described above for the molecular subunits. Assays useful in determining biological activity include, for example, binding assays; assays to determine changes in biological target function, cellular physiology, cellular viability, and cellular growth characteristics; immunological assays; and assays to determine alteration of nucleic acid and protein expression.

In a preferred embodiment, an initial screen for biological activity of a recombined molecule comprises contacting the recombined molecule with a biological target. Examples of biological targets include, but are not limited to, whole cells, cellular extracts, proteins, enzymes, and nucleic acids. As discussed above, a biological target may comprise more than one component.

One embodiment of the invention provides for a method of screening for a recombined molecule capable of binding to a biological target. In preferred binding assays, either the molecular subunit or the biological target is labeled, as described above, to provide a means of detecting the binding of the molecular subunit to the biological target. Alternatively, the molecular subunit can be immobilized or covalently attached to a surface and contacted with a labeled biological target.

Another embodiment provides for methods of screening for a biologically active recombined molecule that modulates a property of a biological target. Assays useful in screening for biologically active recombined molecules that modulate a property of a biological target include cell growth and mortality assays (including assays to determined antimicrobial and antiproliferative activity), whole organism growth and mortality assays, protein binding assays, enzyme inhibition/activation assays, immunological assays, biochemical assays, and transcription and translations assays.

Another embodiment provides for screening for recombined molecule(s) which modulate expression levels of genes using methods described above and other methods well know in the art.

As set forth above, the invention provides for methods of cleaving a starting molecule or starting molecules into molecular subunits and assembling all or some of the resulting molecular subunits to produce a recombined molecule or recombined molecules. In one embodiment, at least one of the cleaving or assembling steps is mediated by an enzyme. In another preferred embodiment, at least one of the cleaving or assembling steps is mediated by an enzyme and at least one of the cleaving or assembling steps is not mediated by an enzyme. In another embodiment, both the cleaving and assembly steps are mediated by an enzyme. In yet another embodiment, neither cleavage nor assembly is mediated by an enzyme.

As discussed above, enzymes useful in the cleaving of molecules include, but are not limited to, enzymes involved in group transfer reactions, hydrolases, oxidases, reductases, proteases, peptidases, esterases, mono-oxygenases, enzymes involved in substitution reactions, enzymes involved in electrophilic or nucleophilic addition, and enzymes involved in decarboxylation. Examples of enzymes useful in this group comprise pig liver esterase (PLE), horse liver esterase (HLE), acetylcholine esterase (ACE), carbonylesterase NP, alpha-chymotrypsin, subtilisin, trypsin, pepsin, papain, penicillin acylase, porcine pancreatic lipase (PPL), formate dehydrogenase (FDH), ethanol and alcohol dehydrogenase (ADH), yeast alcohol dehydrogenase (YADH), horse liver alcohol dehydrogenase (HLDH), glucose dehydrogenase (GDH), enolate reductases, oxidoreductases, mono-oxygenases including cytochrome p450 dependent mon-oxygenases and flavin-dependent mono-oxygenases, soybean lipoxygenase, alpha oxidases, aldehyde dehydrogenases, horseradish peroxidase, chloroperoxidase (CPO), bromoperoxidases, etc. The enzymes used to cleave the molecule may be purified enzymes, enzyme extracts or may be present in whole cells. Chemical reactions useful for cleaving bonds include, but are not limited to, chemical hydrolysis, reductions, oxidations, ozonolysis, decarboxylation, electrophilic additions, nucleophilic additions, etc. Enzymes useful in mediating the assembly of molecular bonds include lyases, comprising aldolases, transketolases, hydroxynitrile lyases, and enzymes that mediate acyloin reactions. Additional enzymes useful in mediating the assembly of molecular bonds include ligases, fumarases, glycosyl transferases, glycosidases, haloperoxidases and halohydrin eposidases. Nonenzymatic tools useful for molecular subunit assembly include non-mediated chemical reactions and reactions mediated by chemical agents such as coupling reagents or chemical cross-linkers.

The cleaving of the starting molecules, or of molecular subunits, can be performed simultaneously, for example with the use of multiple enzyme systems. Alternatively, the cleaving steps can be performed sequentially, allowing for use of different enzymes to produce molecular subunits. In this embodiment, the starting molecules are cleaved with one enzyme or set of enzyme and the resulting molecular subunits split into pools and cleaved with a different enzyme or set of enzymes.

Similarly, the assembly of the molecular subunits into recombined molecules can be performed simultaneously, for example with the use of multiple enzyme systems. Alternatively, the assembly steps can be performed sequentially, allowing for use of different enzymes to produce recombined molecules.

In a preferred embodiment, the cleaving of the starting molecules and assembly of the recombined molecules is performed ex vivo.

Starting Molecules

The starting molecules useful in the methods described herein are selected on the basis of several features. In a preferred embodiment, the starting molecules are easily synthesizable or readily available, they contain multiple reactive sites when cleaved so that molecular subunits can be added to form recombined molecules, and they possess the potential for stereochemical diversity. In some embodiments, the starting molecule has biological activity. Particularly preferred embodiments include the use of starting molecules with antimicrobial, antineoplastic, antiinfective, or antiproliferative activity.

In one embodiment of the invention, one starting molecule is cleaved to form molecular subunits. In a preferred embodiment of the invention, at least two different starting molecules are cleaved to form molecular subunits. In a further preferred embodiment, at least three different starting molecules are cleaved to form molecular subunits. In yet further embodiments, four, five, or greater than five different starting molecules are cleaved to form molecular subunits. In all of the embodiments, the molecular subunits may be analyzed to identify the structure or biological activity of the molecular subunits or may be assembled to form recombined molecules.

In a preferred embodiment, at least one of the starting molecules is selected from the group consisting of small molecules, polypeptides, peptidomimetics, nucleic acids, alkaloids, macrolides, terpenes, macrocycles, fermentation products, or molecules from plant, animal, bacterial, or fungal sources. The term "small molecule" refers to an organic compound either synthesized in the laboratory or found in nature. Typically, a small molecule is characterized in that it contains several carbon-carbon bonds, and has a molecular weight of less than 1500, although this characterization is not intended to be limiting for the purposes of the present invention. Examples of "small molecules" that occur in nature include, but are not limited to, taxol, dynemicin, rifamycins (including Rifamycin B), rapamycin, camptothecin, vancomycin, erythromycins, 9-hydroxyellipticine, bisamidophthalanide derivatives, actinomycinD, avermectin B1, phomopsin A, and cytochalasin D.

By "polypeptides" or grammatical equivalents herein is meant proteins, oligopeptides and peptides, derivatives and analogs, including proteins containing non-naturally occurring amino acids and amino acid analogs, and peptidomimetic structures. The side chains may be in either the (R) or the (S) configuration. In a preferred embodiment, the amino acids are in the (S) or L-configuration.

Generally, a "nucleic acid" may refer to either DNA or RNA, or molecules which contain both deoxy- and ribonucleotides. The nucleic acids include genomic DNA, cDNA and oligonucleotides including sense and anti-sense nucleic acids. The nucleic acid may be double stranded, single stranded, or contain portions of both double stranded or single stranded sequence.

In one embodiment, at least one of the recombined molecules is not a recombined nucleic acid or a recombined protein. By "recombined nucleic acid" is meant a DNA or RNA produced by gene shuffling, homologous recombination, or by assembly of oligonucleotides (for example, by ligation). By "recombined protein" or "recombined polypeptide" is meant a polypeptide produced by the formation of a peptide bond between two or more amino acids, between two or more peptides and/or proteins, or between a combination of peptides and amino acids. It also includes polypeptides encoded by the aforementioned recombined nucleic acid. However, starting molecules may include nucleic acid(s) and/or protein(s) alone or in combination with other starting molecules which are neither nucleic acids nor proteins.

In another embodiment, the starting molecules are not nucleic acids, e.g. DNA and/or RNA. In yet another embodiment, the starting molecules are not polypeptides. Still further, in some embodiments, the starting molecules are neither nucleic acids nor polypeptides.

Libraries

A further aspect of the invention provides for libraries of the molecular subunits or recombined molecules produced by the methods described herein.

Libraries of molecular subunits or recombined molecules may be produced from starting molecules present in a liquid solution or from starting molecules wherein at least one of the starting molecules is attached to a solid support. The synthesis of the libraries from solid support bound starting molecules is particularly preferred. In other embodiments, both liquid and solid phase reactions can be utilized depending on the nature of the libraries, efficiencies and yields desired.

A further aspect of the invention provides for methods of screening the libraries for biological activity. The biological activity of the libraries can be determined by a variety of assays as described above for the molecular subunits and recombined molecules. Assays useful in determining biological activity include, for example, binding assays; assays to determine changes in biological target function, cellular physiology, cellular viability, and cellular growth characteristics; immunological assays; and assays to determine alteration of nucleic acid and protein expression.

In a preferred embodiment, an initial screen for biological activity of a library comprises contacting the library with a biological target. Examples of biological targets include, but are not limited to, whole cells, cellular extracts, proteins, enzymes, and nucleic acids. As discussed above, a biological target may comprise more than one component.

One embodiment of the invention provides for a method of screening a library for members capable of binding to a biological target. In preferred binding assays, either the members of the library or the biological target is labeled, as described above, to provide a means of detecting the binding of the molecular subunit to the biological target. Alternatively, the library members can be immobilized or covalently attached to a surface and contacted with a labeled biological target.

Another embodiment provides for methods of screening for biologically active libraries that modulate a property of a biological target. Assays useful in screening for biologically active libraries that modulate a property of a biological target include cell growth and mortality assays (including assays to determined antimicrobial and antiproliferative activity), whole organism growth and mortality assays, protein binding assays, enzyme inhibition/activation assays, immunological assays, biochemical assays, and transcription and translations assays.

Another embodiment provides for screening for libraries which modulate expression levels of genes using methods described above and other methods well know in the art.

Samples retrieved before, during and after various enzymatic or chemical reactions can be studied for biological activity in a broad series in vitro and in vivo of assays including protein binding, biochemical, immunological, cellular, animal models gene and protein expression after cellular exposure with test chemical samples, including gene and protein expression chips.

In a preferred embodiment, the members of a library are purified and screened for biological activity as described above to identity the members that are biologically active. In a further preferred embodiment, the biologically active members are isolated and analyzed for chemical structure and biological properties as discussed above.

The present invention additionally provides pharmaceutical compositions containing one or more of the recombined molecules produced by the methods herein. In a preferred embodiment, the pharmaceutical composition preferably comprises one or more of the recombined molecules and a pharmaceutically acceptable carrier using formulation methods known to those of ordinary skill in the art. These formulations can be administered by standard routes. In general, the compounds may be administered orally, intravenously, topically, intravescularly, intraperitoneally, intramuscularly, intradermally, subcutaneously or intraarterially.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes.

EXAMPLES

Example 1

Production of Recombined Molecule from One Starting Molecule-General Example

Chemical cleavage or enzymatic digestion of a starting molecule provides a mixture of several known fragments or molecular subunits (FIG. 1. A, B and C). The molecular subunits from this pool are evaluated for their biological properties and/or use as building blocks to generate large libraries of structurally complex products via the production of recombined molecules.

The mixture of molecular subunits is subsequently split in two pools. The subunits of each pool are blocked at a specific site by either the protection group P and protection group Q. This results in two different molecular subunit pools, which are longer able to react with themselves. Mixing of the two pools under the proper conditions results in a well defined mixture of novel protected recombined molecule products. Deprotection of the entire mixed pool with a reagent chemically, enzymetically or photochemically, provides the final mixture of novel unnatural recombined molecules. A variation of the above method involves placing one of the protection groups (P or Q) on a solid phase resin (e.g. polystyrene). The "pure" recombined products are then liberated from the resin by hydrolysis, photochemical reaction, or other means.

Example 2

Production of Recombined Molecule from One Starting Molecule-Vancomycin

Intramolecular Recombination of Vancomycin

Figure 2:
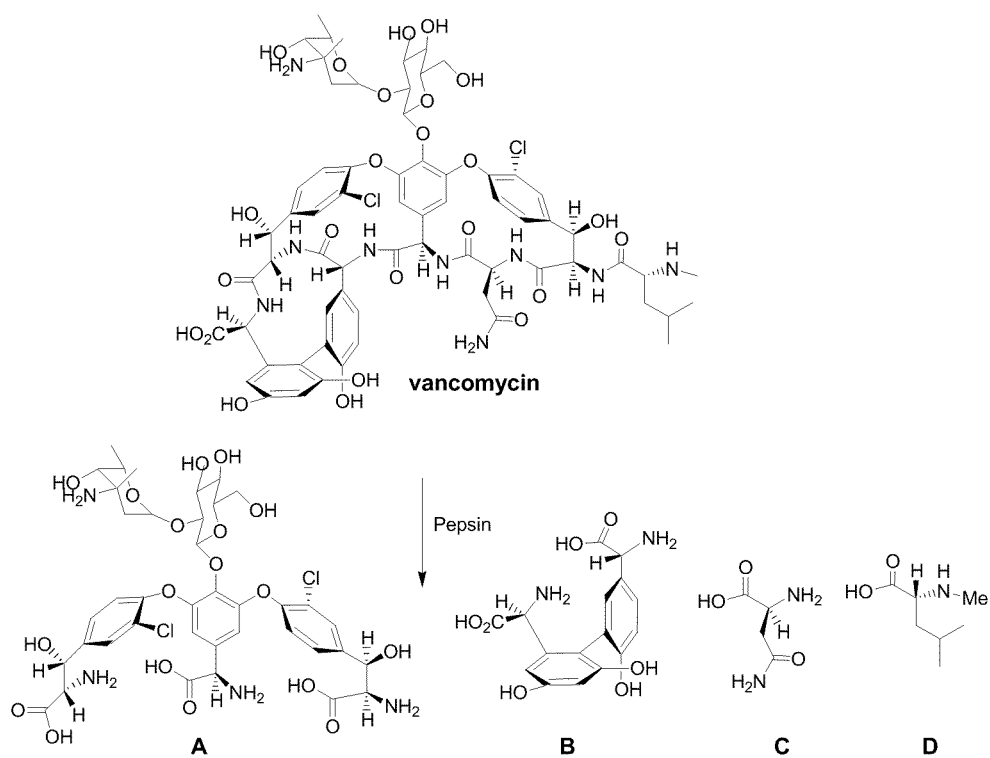
FIG. 2 depicts the enzymatic cleavage of vancomycin with pepsin and the resulting molecular subunits.
Figure 3A:
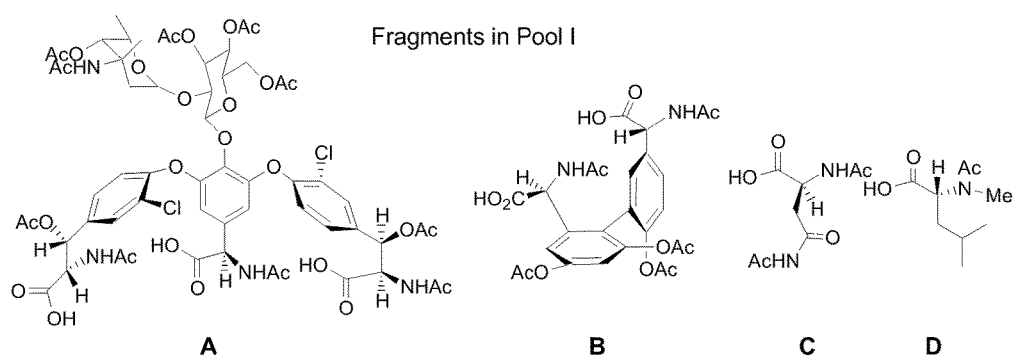
FIG. 3A depicts vancomycin molecular subunits (Pool I) after treatment with acetic anhydride (or any other acylation reagents that will acylate all alcohols and amino groups).
Figure 3B:
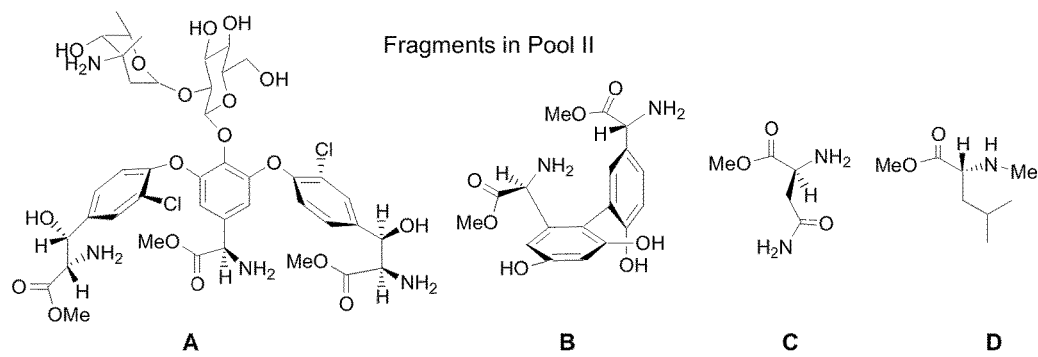
FIG. 3B depicts vancomycin subunits (Pool II) after treatment with methylating agents (TMSCHN$_2$, AcCl/MeOH or any other chemical or enzymetic methylating procedures).

Cleavage of vancomycin with pepsin or other proteases provides a mixture of molecular subunits (FIG. 2). The mixture containing the molecular subunits is split in two separate pools: Pool I and Pool II. Pool I is treated with acetic anhydride or any other acylation reagents that acylate all alcohols and amino groups to yield the products shown in FIG. 3A.

Pool II is exposed to methylating conditions (TMSCHN$_2$, AcCl/MeOH or any other chemical or enzymetic methylating procedures) for several hours. These conditions ensure methylation of all the carboxylic acid moieties present to yield the fractions shown in FIG. 3B.

Addition of the commercially available solid phase bound peptide coupling reagents (such as the carbodiimide EDCI) or any other peptide coupling reagent promote the condensation of any amine with any free (unblocked) carboxylic acid. A general reaction of two amino acids is shown below. The advantage of using a polymer bound reagent is the ease of separating the products from the reagents by simple filtration, however the use of solid bound reagents is not a requirement.

Mixing of Pool I with Pool II in the presence of polymer bound coupling reagent (such as a carbodiimide) randomly couples each acylated vancomycin molecular subunit of Pool I with each methylated vancomycin molecular subunit of Pool II. After hydrolysis of the new mixture with NaOH, all protection groups (P and Q) are removed simultaneously and the resulting products are a known mixture of 64 ($4^4$) novel vancomycin derived products. Alternatively, either one of the protection groups (P or Q) could be resin bound to facilitate the isolation of the products form the solvent/reagents by filtration.

Example 3

Production of Recombined Molecule from Two Starting Molecules-Vancomycin and Rifamycin B Intermolecular Recombination of Vancomycin and Rifamycin B The same methodology used for intramolecular recombination is applied to a mixture of two starting molecules. For example, the inexpensive commercially available RNA polymerase inhibitor rifamycin B (~$50/gram, Sigma) and vancomycin (~$100/gram, Sigma) is recombined intermolecularly to generate a library of high complex hybrid agents.

Figure 4:
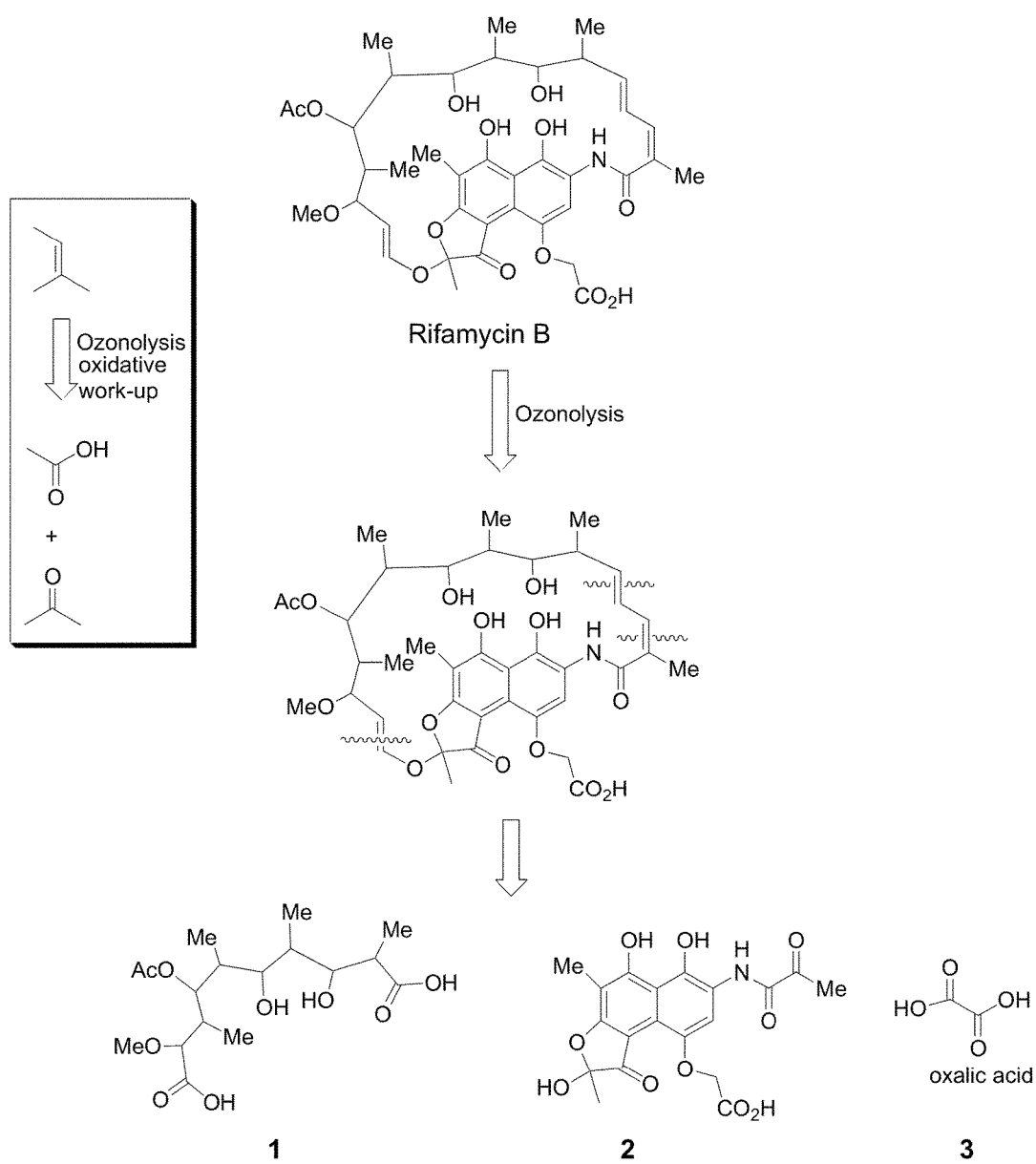
FIG. 4 depicts cleavage of rifamycin B into three products with fraction 1 containing two carboxylic acids, fraction 2 containing one carboxylic acid and fraction 3 containing oxalic acid.
Figure 5:
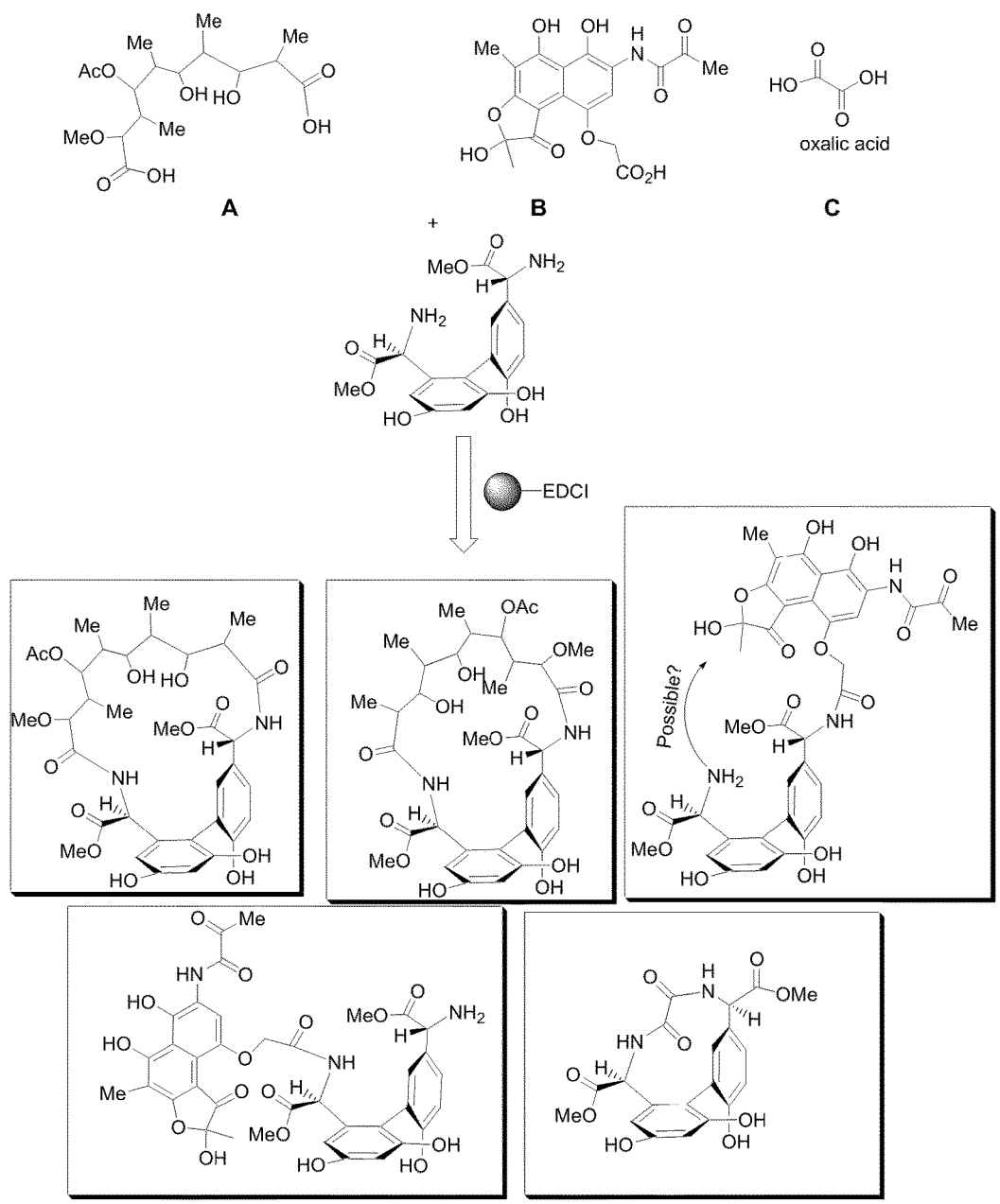
FIG. 5 depicts recombined molecules produced from rifamycin B fragments (FIG. 4, fragments 1-3) and fraction B of Pool 2 (FIG. 3B).
Figure 6:
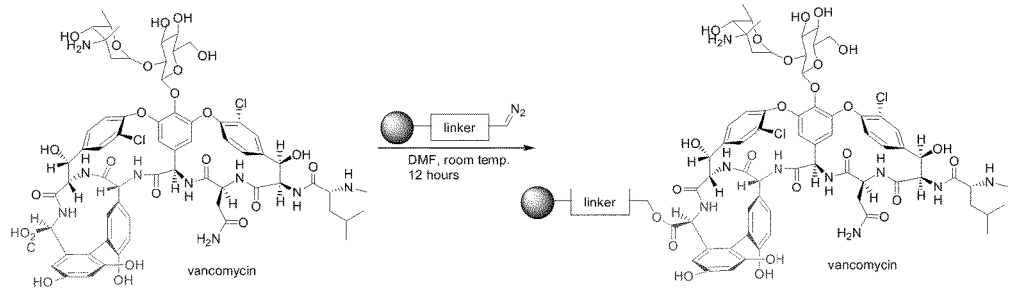
FIG. 6 depicts the production of recombined molecules from resin-bound Vancomycin and Rifamcyin B molecular subunits.
Figure 6:
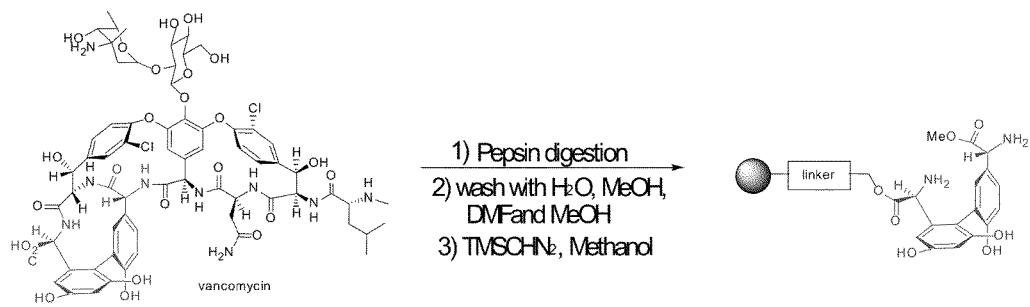
Figure 6:
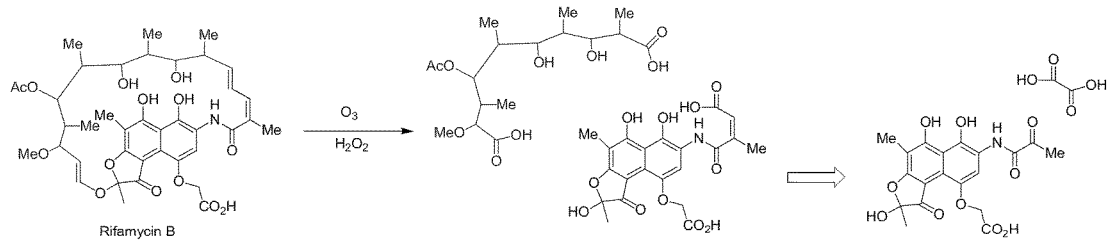
Figure 6:
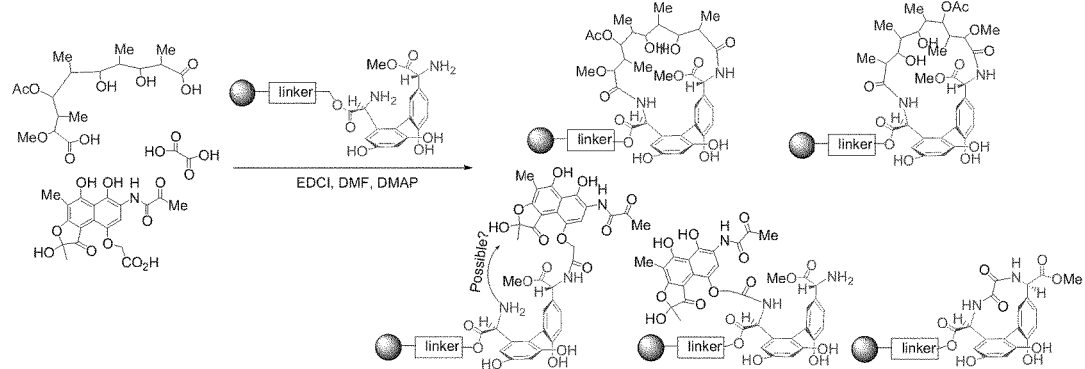
Figure 6:
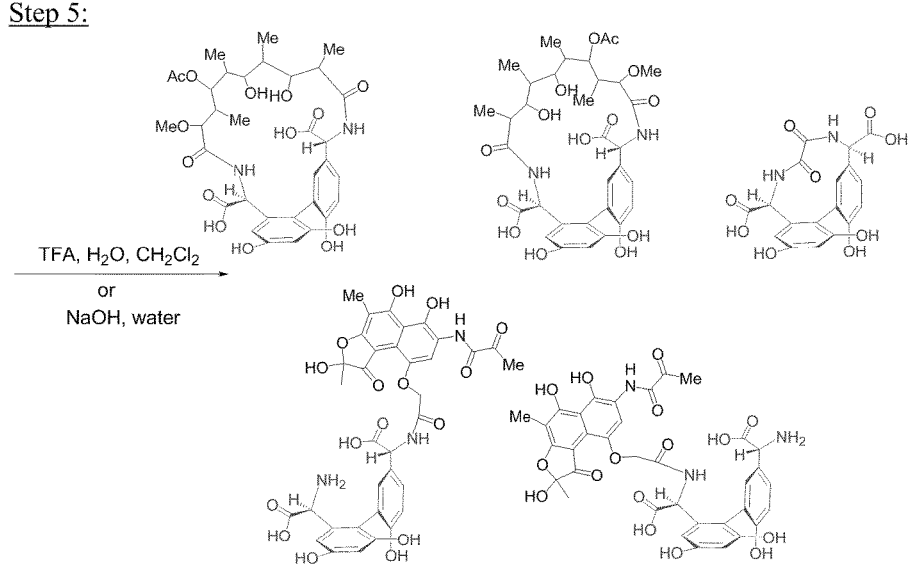

Cleavage of rifamycin B provides a mixture of three products with fraction 1 containing two carboxylic acids, fraction 2 one carboxylic acid and fraction 3 is oxalic acid (FIG. 4). Treatment of this mixture with the vancomycin mixture from Pool 2 (FIG. 3B) provides a library of highly complex unnatural products that can be evaluated for biological activity.

Alternatively, fraction B of Pool 2 (FIG. 3B) is isolated to simplify the reaction. Treatment of the rifamycin B fragments (FIG. 4, fragments 1-3) with fraction B of Pool 2 (readily isolated by HPLC or other chromatographic separation) provides a mixture of compounds shown in FIG. 5. As illustrated by the structural complexity of the compounds formed, the direct synthesis of each of these products via conventional chemistry would be a significant endeavor. One advantage of the methods described herein is the immediate access to a library of highly complex hybrid compounds otherwise not accessible. The products available from the recombination of fraction A from Pool II (FIG. 3B) provides an additional library of complex unnatural products.

Exemplary Procedure

Step 1:

To readily isolate one of the vancomycin molecular subunits of interest, the region of interest is linked to a solid support. In this example, a diazosubstituted polystyrene resin support is used. (FIG. 6). 500 mg Vancomycin is added to a solution of dimethylformamide containing 2 grams of the diazosubstituted polystyrene resin. The mixture is stirred overnight at room temperature. The resin is filtered off and the filtrate is examined for the amount of remaining "unreactive" vancomycin.

Step 2:

The resin-linked vancomycin is subsequently treated with an excess of pepsin or trypsin overnight at 37° C. to ensure complete digestion of all peptide bonds. After complete digestion, the resin is filtered off and washed with water followed by methanol, dimethylformamide, and once again methanol to elude all the pepsin, peptide fractions and other vancomycin subunits. The product here is the single vancomycin subunit attached to the solid support resin. The resin is subsequently added to a solution of methanol (5 mL) and 1 mL 2M trimethylsilyl diazomethane is added. The reaction is stirred for 1 hour after which the resin is filtered off again. The product on the resin is now blocked at the carboxylic acid end with a methyl group.

Step 3:

The rifamycin molecule is prepared via standard ozonolysis (Chemical Reviews 1958, 58, 925). 500 mg Rifamycin is added to a round bottom flask containing 10 mL dichloromethane at −78° C. Ozone is bubbled through the solution for 30 minutes after which 2 mL of a 50% hydrogen peroxide solution is added. The mixture is allowed to warm to room temperature and the entire solution is evaporated to dryness. The products from this reaction are the corresponding carboxylic acids for each of the non-aromatic double bonds. All reagents used in this reaction are volatile and can be evaporated off. The entire product mixture is used in the next step where the reagents are coupled with the vancomycin subunit—bounded resin.

Step 4:

The rifamycin mixture is redissolved in 10 mL dimethyl formamide and 15 equivalents of the carbodiimide EDCI is added followed by 15 equivalents of dimethylaminopyridine and the vancamycin substituted resin. The whole mixture is allowed to stir overnight at room temperature. The next morning the resin is isolated again by simple filtration and all reagents and potential side products are wash off the resin.

Step 5:

The final products are cleaved off the resin by treating the resin with either 10% trifluoroacetic acid and 10% water in dichloromethane or by treatment of the resin with NaOH in water. Both reactions will also remove the methyl group used in step b. The resin is filtered off and the filtrate will contain five new complex unnatural scrambled products.

Example 4

Production of Recombined Molecule from Two Starting Molecules-Intramolecular Recombination of Carbohydrate Groups Many antitumor agents and antibiotics have a variety of carbohydrate groups, which aids the activity as well as the pharmacological profile of these agents. Several classic examples include; etoposide, and analogues, doxorubicin and analogues, mithramycins and analogues, phleomycins (bleomycin), vancomycin etc. In many cases hundreds of analogues have been prepared of these drugs to increase their pharmacological profile. In the case of simple carbohydrates (etoposide) SAR studies are readily accessible. In the case of more complex molecules and carbohydrates (vancomycin) SAR studies require non-combinatorial, long and tedious syntheses (K. C. Nicolaou, Chem. Eur. J. 2001, 7, 3798-3823, herein incorporated by reference).

Figure 7:
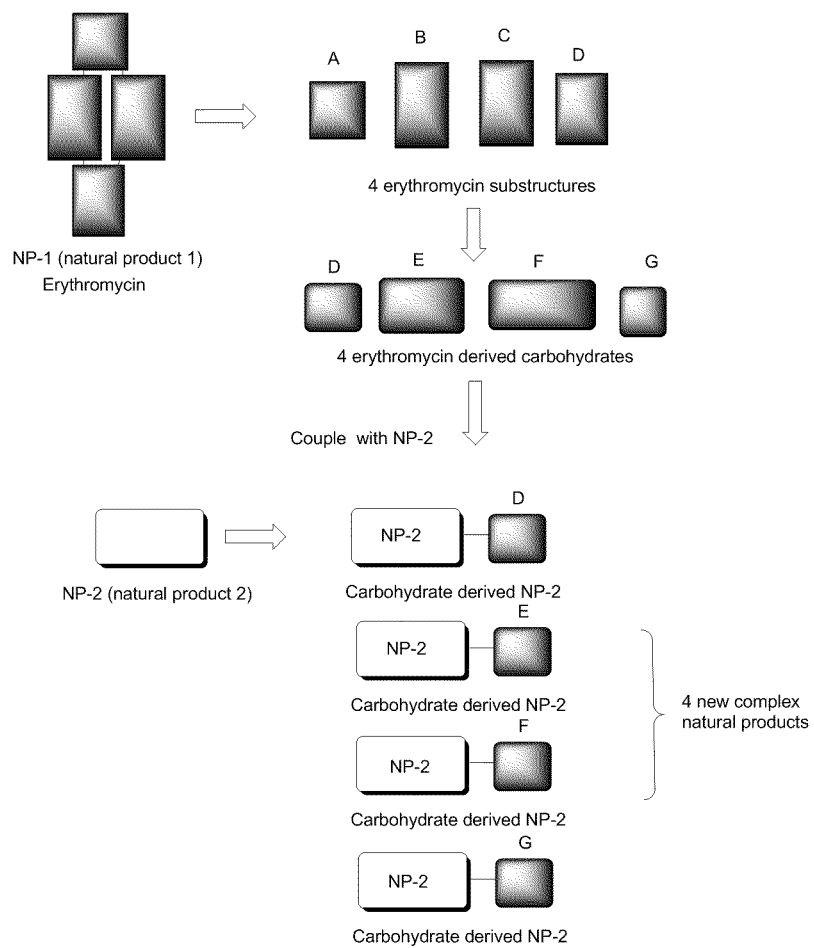
FIG. 7 depicts a general scheme for the production of recombined molecules from molecular subunits derived from assembling the molecular subunits from one starting molecule (NP-1) with a second molecule (NP-2).

The methods described herein will take advantage of nature's enantioselective synthesis of complex natural product to readily prepare a library of complex carbohydrates subunits. These structures can be generated from the degradation of cheap, readily available natural products (for example, but not limited to erythromycin, Aldrich Co. QW). The corresponding subunits can be used to rapidly prepare new complex analogues of other agents to optimize their pharmacological profile. A general schematic is shown in FIG. 7 followed by a more detailed description.

Figure 8:
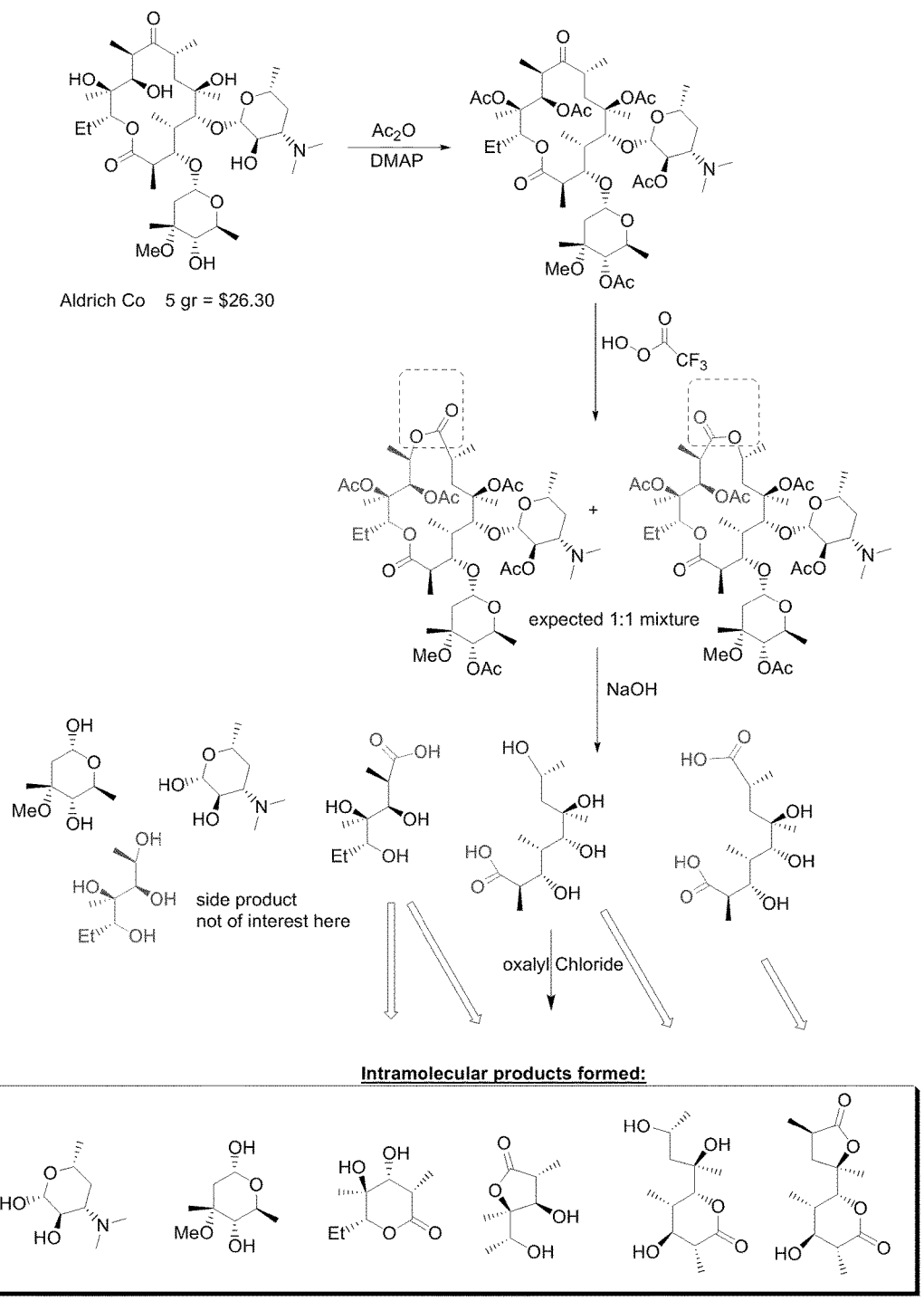
FIG. 8 depicts the cleavage of a natural product (NP-1), such as erythromycin, into molecular subunits.
Figure 9:
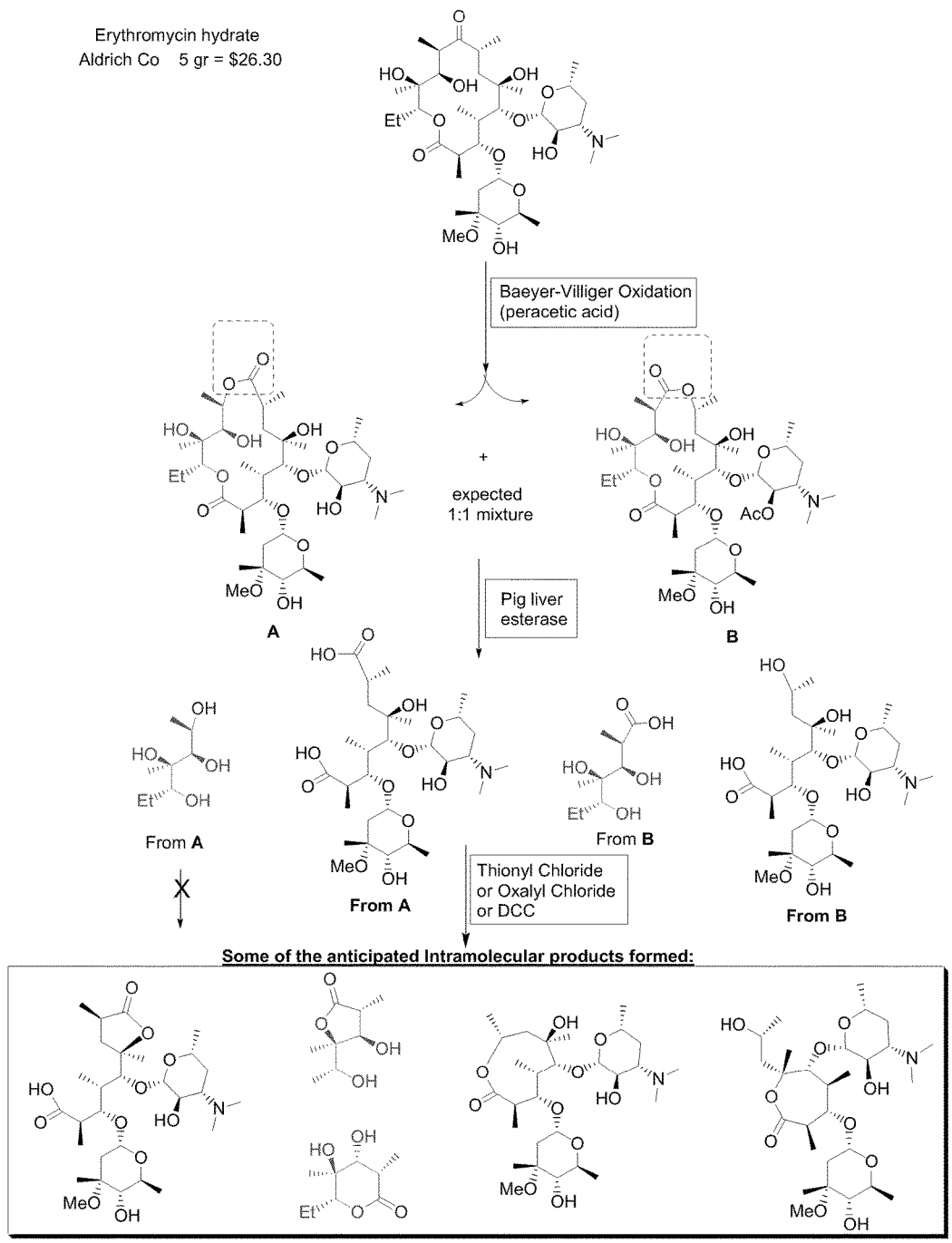
FIG. 9 depicts the cleavage of a natural product (NP-1), such as erythromycin, into molecular subunits.

In FIG. 8 a starting molecule such as erythromycin (abbreviated by NP-1, natural product 1) or semi-synthetic or modified natural product, compound, structure or scaffold is cleaved to form several molecular subunits. These subunits can be tested for their biological activity and/or used to generate recombined molecules. These first generation fractions can be enzymatically or chemically treated to yield a mixture of a second generation of complex products. These agents are purified by HPLC and characterized or left as a mixture. Several rounds of cleavage steps are used to generate subsequent generations of complex subunit products (FIG. 8). Many different erythromycin-type macrocycles have now been isolated or prepared and are commercially available. Starting with different derivatives of erythromycin will produce different products. In addition, by simply changing the original first step a completely different variety of products can be generated from erythromycin. A specific example is shown in FIG. 9.

Representative procedure (see FIGS. 8 & 9):

Protection of the hydroxyl groups by acetate groups provides the fully protected erythromycin in near quantitative yields. A chemically mediated Baeyer-Villiger oxidation with trifluoroperoxyacetic acid (or enzymatically mediated Baeyer-Villiger oxidation using engineered baker's yeast, Current Opinion in Biotechnology, 2000, 11, 363-368, herein incorporated by reference) yields the corresponding esters. Other Bayer-Villiger type oxidations can be used as well. The resulting products can be immediately tested for their biological activity and/or used in further functional group manipulations.

Chemical cleavage of all esters by base (or an esterase Organic Process Research & Development 2002, 6, 441-445) produces the several major erythromycin fragments. If base is used both carbohydrates are cleaved off as well. Treatment of the crude mixture with a coupling reagent such as oxalyl chloride (or dicyclocarbodiimide and many other possibilities), provides the shown major five and six membered intramolecular recombined molecules. These products (other minor products are also possible) are purified by HPLC or left as a mixture of products and can be tested for their biological activity and/or further scrambling.

Figure 10:
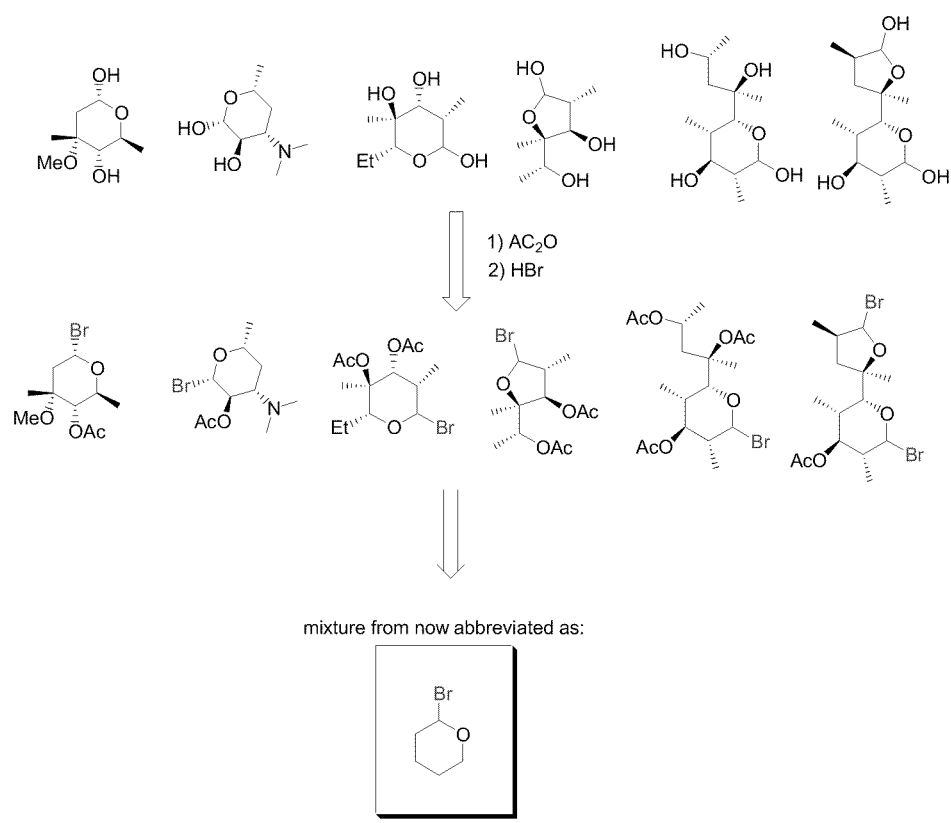
FIG. 10 depicts the bromination of molecular subunits derived from cleavage of erythromycin.

The molecular subunits that originated from erythromycin can be modified to serve as functional groups of other natural products. Reduction of the corresponding lactones from the degradation of erythromycin (FIG. 8) with sodium borohydride (or diisobutyl aluminum hydride [DIBAL]), or alternatively with a reductase, produces a library of highly complex carbohydrates (FIG. 8). The complex carbohydrate library are subsequently tested for their activity on their own and/or used to produce recombined molecules. Protection of the hydroxyl groups by acetic anhydride, or any other appropriate protection group procedure, followed by treatment of the mixture with HBr in acetic acid will provide the bromide in the anomeric position (C-1) according to standard protocol (FIG. 10). Other potential activation groups on the anomeric carbon can be used as well.

NP-2, a second starting molecule (vancomycin or any other natural product, semi-synthetic or modified natural product, compound, structure or scaffold) can be coupled to the carbohydrates (recombined molecules or molecular subunits produced from erythromycin) to provide a library of structurally diverse and complex recombined molecule products. Any agent with a nucleophilic site such as, but not limited to, a hydroxyl group (—OH) or an amine group (—NH$_2$) can be coupled with the carbohydrate recombined molecules.

The carbohydrate templates can be coupled with any nucleophilic agent, natural product, semi-synthetic or modified natural product, compound, structure or scaffold. Representative nucleophiles may include, but are not limited to, simple natural products, or other pharmaceutical agents such as the podophyllotoxins, 9-aminoacridines, doxorubicins or camptothecins (for an illustrative example using anticancer agent camptothecin, see FIG. 11).

Figure 11A:
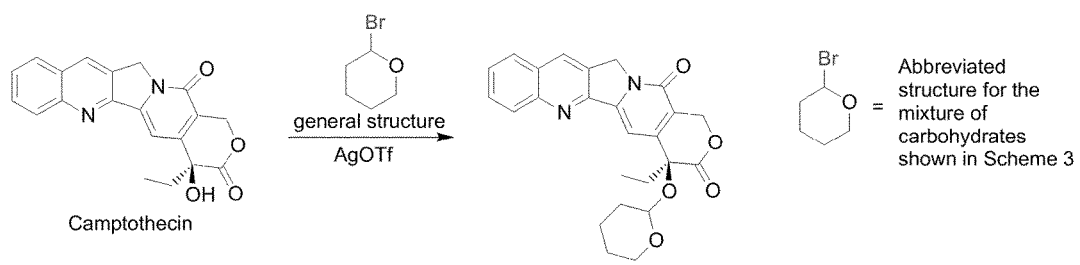
FIG. 11A depicts the coupling of brominated molecular subunits derived from cleavage of erythromycin with camptothecin.

In addition to the functionalization of known glycosidated natural products, new glycosidated products can also be prepared to enhance their pharmacological profile (FIG. 11). Two representative examples are 9-hydroxyellipticine and bisamidophthalaniline.

Figure 11B:
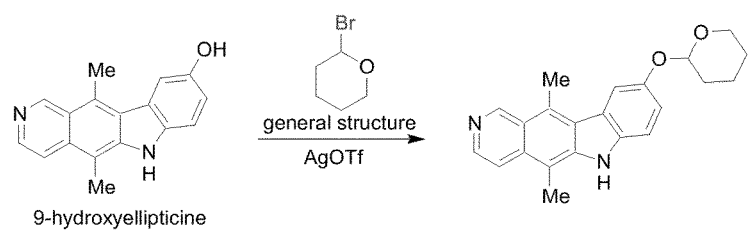
FIG. 11B depicts the coupling of brominated molecular subunits derived from cleavage of erythromycin with 9-hydroxyellipticine.

9-Hydroxyellipticine is the metabolic product from ellipticine and lacks the related hemolysis toxicity found in ellipticine at therapeutic dosage. Glycosidation of 9-hydroxyellipticine might therefore improve its pharmacological profile even more (similar to the development of etoposide from podophyllotoxin) (FIG. 11B).

Figure 11C:
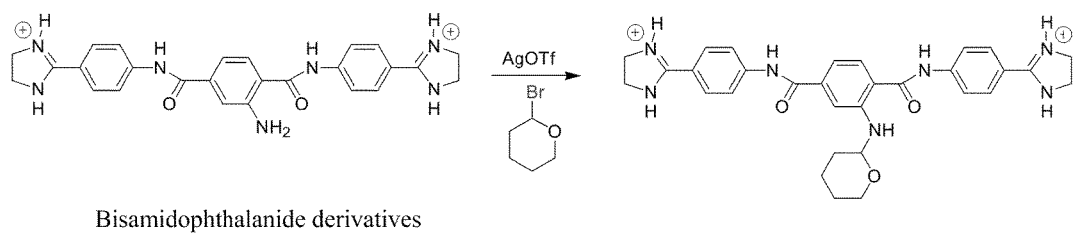
FIG. 11C depicts the coupling of brominated molecular subunits derived from cleavage of erythromycin with bisamidophthalanide.

Similarly, coupling of the activated carbohydrates from the erythromycin library will produce a new library of glycosidated bisamidophthalanilides derivatives (FIG. 11C).

Figure 12:
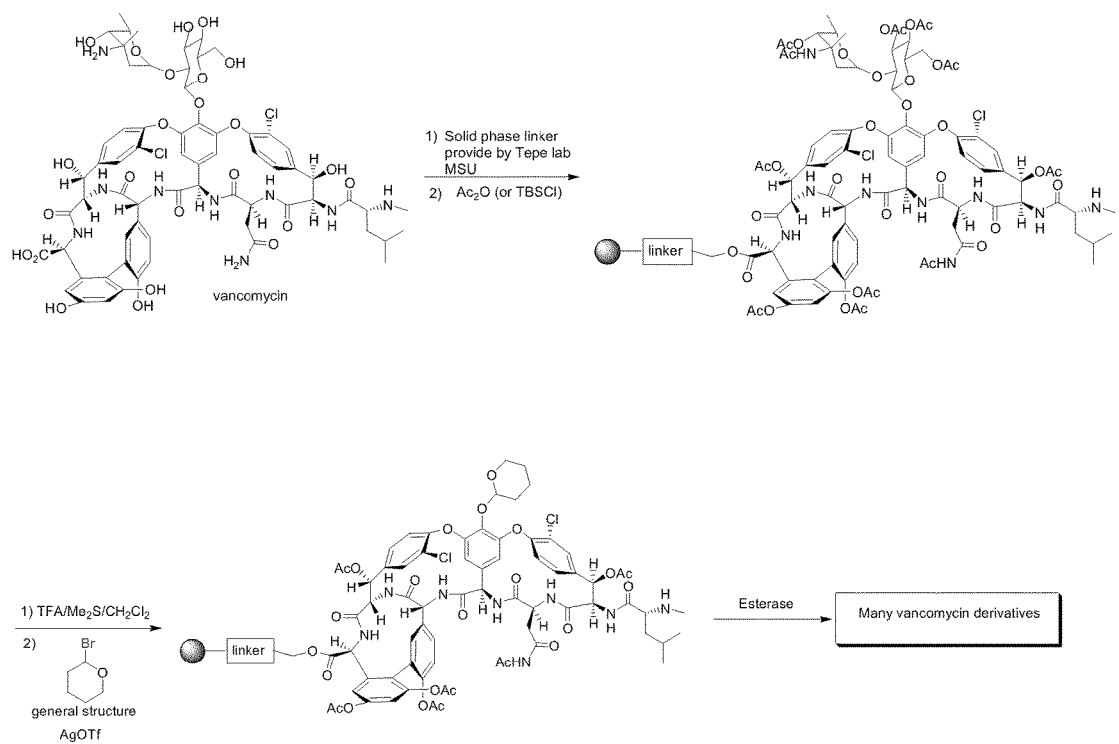
FIG. 12 depicts the production of recombined molecules from vancomycin bound to a solid support.
Figure 13:
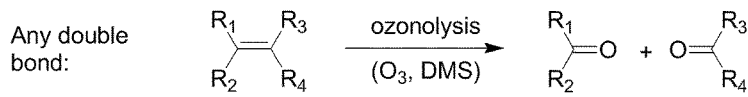
FIG. 13 depicts examples of reactions useful producing molecular subunits and recombined molecules.
Figure 13:
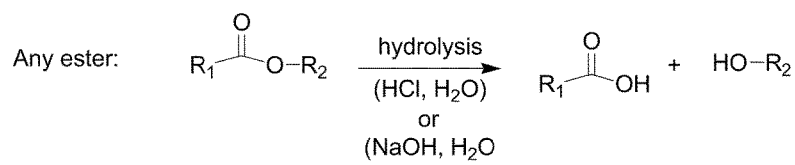
Figure 13:
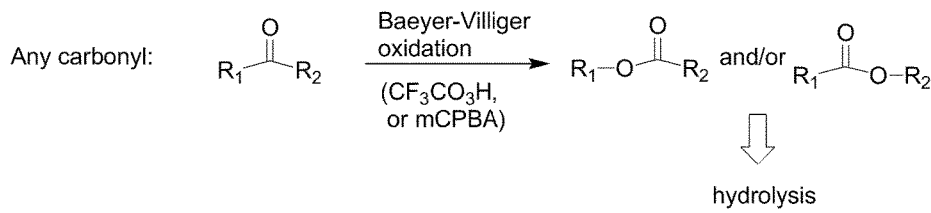
Figure 13:
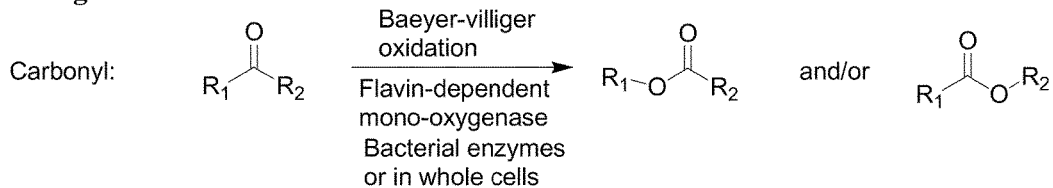
Figure 13:
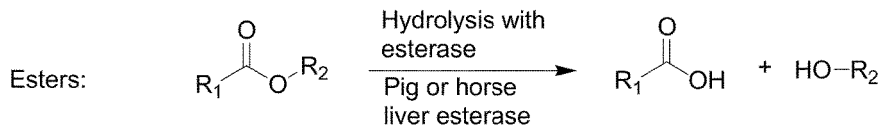
Figure 13:
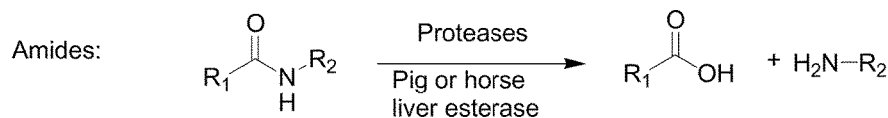

Other complex natural products such as, but not limited to, vancomycin can modified by this new library of recombined molecules. To facilitate the purification process the starting molecule can be bound to a solid phase first (for a representative example see FIG. 12). The resin bound starting molecules can be exposed to the library of the carbohydrates (recombined molecules or molecular subunits from erythromycin) to produce new glycosidated vancomycin-type molecules. Cleavage of the final product from the bead chemically (NaOH) or enzymatically (esterase) will render new vancomycin analogues (FIG. 12).

Additional commercially available representative structures for creation of unique and complex molecular structures are shown below. These compounds are representative examples and the invention is not limited to the structures described but includes all complex natural products, semi-synthetic or modified natural products, compounds, structures or scaffolds.

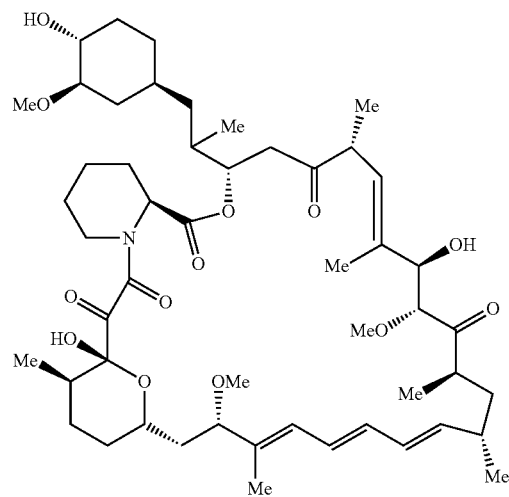

Rapamycin ~1 mg/$100
Antifungal and immunosuppressant
Within same class: FK-506 amd Ascomycin (FR-900520)

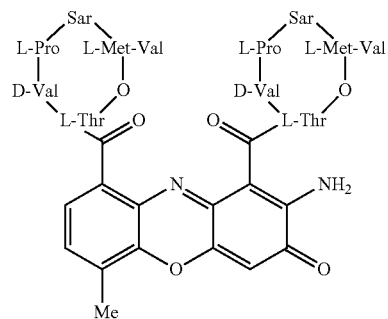

Actinomycin D, *Streptomyces* sp.
Antineoplastic antibiotic
~10 mg/$100

-continued
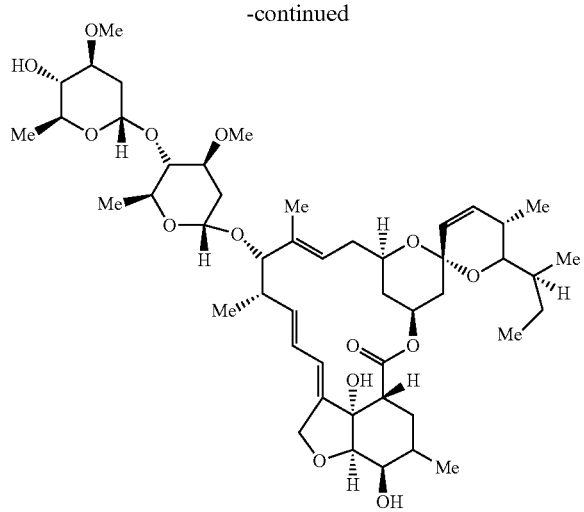
Avermectin B1, *Streptomyces avermitilis*
(Abamectin) ~100 mg/$100
Anthelmintic and pesticidal properties
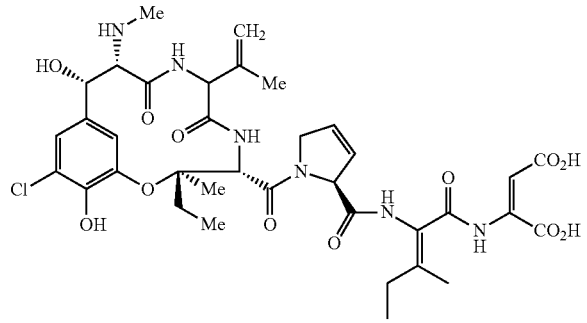
Phomopsin A, *Phomopsis leptostromiformis*
(PMSA) Inhibitor of microtubuline assembly
~1 mg/$200
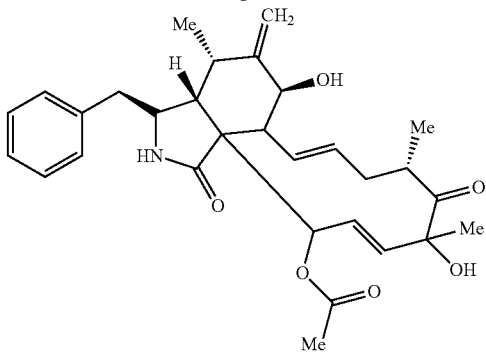

Cytochalasin D, *Zygosporium mansonii*
Cell-permeable fungal toxin. Inhibits cyctoplasmic division
Contains antitumor activity.
1 mg/$100
Other members of this class Cytochalasin A-E

Example 5

Screening for Antimicrobial Activity

The following Gram-negative and Gram-positive bacteria that can be screened for antimicrobial activity include but are not limited to: *Staphylococcus aureus, Enterobacter aerogenes, Escherichia coli, Klebsiella pneumonia, Pseudomanas aeruginosa, Serratia marcescens, Bacillus cerius, Bacillus subtillus* and *Micrococcus luteus*. Bacterial isolates are removed from storage, streaked on to nutrient agar plates and incubated for 18-24 hours at 35° C. A working bacterial suspension is prepared by suspending 3-5 isolated colonies in 5 mL saline solution. The turbidity of this suspension is carefully adjusted photometrically to equal that of a 0.5 McFarland standard. The zone diameters were determined by a standardized disk diffusion method using cation-supplemented Mueller-Hinton agar according to NCCLS guidelines (in National Committee for Antimicrobila Disk Susceptibility Tests-Eighth Ed.: Approved Standard M2-M8. NCCLS, Villanova, Pa., USA). Minimum inhibitory concentrations (MICs) are considered the lowest concentration that give a clear zone of inhibition. The inoculated agar plates are incubated for 16-20 hours at 35° C. in ambient air. The diameters of the zone sizes are read in millimeters. Test agents are administered to disks which are placed on the agar. Diffusion through the agar result in a zone of inhibition.

Additional screening can may include: members of the genus *Streptococcus, Staphylococcus, Bordetella, Corynebacterium, Mycobacterium, Neisseria, Haemophilus, Actinomycetes, Streptomycetes, Nocardia, Enterobacter, Yersinia, Fancisella, Pasturella, Moraxella, Acinetobacter, Erysipelothrix, Branhamella, Actinobacillus, Streptobacillus, Listeria, Calymmatobacterium, Brucella, Bacillus, Clostridium, Treponema, Escherichia, Salmonella, Kleibsiella, Vibrio, Proteus, Erwinia, Borrelia, Leptospira, Spirillum, Campylobacter, Shigella, Legionella, Pseudomonas, Aeromonas, Rickettsia, Chlamydia, Borrelia* and *Mycoplasma*, a member of the species or group, Group A *Streptococcus*, Group B *Streptococcus*, Group C *Streptococcus*, Group D *Streptococcus*, Group G *Streptococcus, Streptococcus pneumoniae, Streptococcus pyogenes, Streptococcus agalactiae, Streptococcus faecalis, Streptococcus faecium, Streptococcus durans, Neisseria gonorrheae, Neisseria meningitidis, Staphylococcus aureus, Staphylococcus aureus* strain RN4220, *Staphylococcus epidermidis, Corynebacterium diptheriae, Gardnerella vaginalis, Mycobacterium tuberculosis, Mycobacterium bovis, Mycobacterium ulcerans, Mycobacterium leprae, Actinomyctes israelii, Listeria monocytogenes, Bordetella pertusis, Bordatella parapertusis, Bordetella bronchiseptica, Escherichia coli, Shigella dysenteriae, Haemophilus influenzae, Haemophilus aegyptius, Haemophilus parainfluenzae, Haemophilus ducreyi, Bordetella, Salmonella typhi, Citrobacter freundii, Proteus mirabilis, Proteus vulgaris, Yersinia pestis, Kleibsiella pneumoniae, Serratia marcessens, Serratia liquefaciens, Vibrio cholera, Shigella dysenterii, Shigella flexneri, Pseudomonas aeruginosa, Franscisella tularensis, Brucella abortis, Bacillus anthracis, Bacillus cereus, Clostridium perfringens, Clostridium tetani, Clostridium botulinum, Treponema pallidum, Rickettsia rickettsii* and *Chlamydia trachomitis*, a unicellular or filamentous eukaryote, a protozoan, a fungus, a member of the genus *Saccharomyces, Kluveromyces*, or *Candida*, and a member of the species *Saccharomyces ceriviseae, Kluveromyces* lactis, or *Candida albicans*.

In Vivo Testing for Antimicrobial Activity

Active agents can tested in vivo following the procedures similar to those described in N. Frimodt-M ller et al., *The Mouse Peritonitis/Sepsis Model*, in Zak et al. (eds) Handbook of Animal models of Infections 127-137 (Academic Press 1999), as well as the studies described in WO 02/090503, both of which are herein incorporated by reference.

All references cited are herein expressly incorporated by reference.

RELEVANT LITERATURE

R. B. Silverman "The Organic Chemistry of Enzyme-Catalyzed Reactions," Academic Press, 2002.

B. A. Bohm, "Introductions to Flavonoids," Harwood Academic Publishers, 1998.

M. Wink, "Functions of Plant Secondary Metabolites and Their Exploitation in Biotechnology," Sheffield Academic Press, 1999.

C. G. Werthmuth, et. al., "Medicinal Chemistry for the 21st Century," Blackwell Scientific Publications, 1992.

National Committee for Clinical Laboratory Standards. *Methods for dilution Antimicrobial Susceptibility Tests for Bacteria that Grow Aerobically*. Fifth Edition: Approved Standard M7-A5. 2000, Wayne, Pa.: NCCLS.

The invention claimed is:

1. A method for preparation of a recombined molecule from vancomycin comprising the steps of:

(a) cleavage of vancomycin with a protease;

(b) splitting the cleaved vancomycin molecules into two separate pools: a first pool and a second pool;

(c) acylating the cleaved vancomycin molecules of the first pool with an acylating agent to acylate all alcohols and amino groups of the cleaved vancomycin molecules of the first pool;

(d) methylating the cleaved vancomycin molecules of the second pool with a methylating agent to methylate all carboxylic acid moieties of the cleaved vancomycin molecules of the second pool;

(e) recombining the acylated cleaved vancomycin molecules of the first pool and the methylated cleaved vancomycin molecules of the second pool by forming peptide bonds with a peptide bond forming agent to afford a recombined molecule from vancomycin comprising acetyl protecting groups and methyl protecting groups; and (f) removing all acetyl protecting groups and all methyl protecting groups present in the recombined molecule from vancomycin in step (e) by base hydrolysis to produce a recombined molecule from vancomycin.

2. A method for preparation of a recombined molecule from rifamycin and vancomycin comprising the steps of:

(a) coupling vancomycin to a solid support, wherein the solid support is a resin;

(b) reacting the vancomycin coupled to the solid support with a protease to hydrolyze the peptide bonds of the vancomycin;

(c) treating all carboxylic acid moieties in the reacted vancomycin of step (b) with a methylating agent to produce methyl-protected vancomycin products;

(d) cleaving rifamycin with ozonolysis to convert non-aromatic double bonds in the rifamycin to carboxylic acids;

(e) reacting the cleaved rifamycin from step (c) with the reacted vancomycin on the solid support from step (c) with a carbodiimide coupling agent;

(f) cleaving the products from step (d) from the solid support; and (g) removing all methyl-protecting groups to produce the recombined molecule from the rifamycin and the vancomycin.

* * * * *